United States Patent
Khouri et al.

(10) Patent No.: US 12,376,874 B2
(45) Date of Patent: Aug. 5, 2025

(54) VIBRATING SURGICAL INSTRUMENT FOR LIPOSUCTION AND OTHER BODY CONTOURING APPLICATIONS

(71) Applicant: Lipocosm, LLC, Key Biscayne, FL (US)

(72) Inventors: Roger K. Khouri, Key Biscayne, FL (US); Khalil R. Khouri, Key Biscayne, FL (US)

(73) Assignee: Lipocosm, LLC, Key Biscayne, FL (US)

( * ) Notice: Subject to any disclaimer, the term of this patent is extended or adjusted under 35 U.S.C. 154(b) by 0 days.

(21) Appl. No.: 18/582,899

(22) Filed: Feb. 21, 2024

(65) Prior Publication Data
US 2024/0268849 A1 Aug. 15, 2024

Related U.S. Application Data

(63) Continuation of application No. 18/196,471, filed on May 12, 2023, which is a continuation of application (Continued)

(51) Int. Cl.
*A61B 17/32* (2006.01)
*A61M 1/00* (2006.01)
(Continued)

(52) U.S. Cl.
CPC ........ *A61B 17/32* (2013.01); *A61B 17/32002* (2013.01); *A61B 17/320068* (2013.01); (Continued)

(58) Field of Classification Search
CPC .............. A61B 17/32; A61B 17/32002; A61B 17/320068; A61B 2017/32007; (Continued)

(56) References Cited

U.S. PATENT DOCUMENTS

| | | |
|---|---|---|
| 3,370,583 A | 2/1968 | Teranishi |
| 5,911,700 A | 6/1999 | Mozsary et al. |

(Continued)

FOREIGN PATENT DOCUMENTS

| | | |
|---|---|---|
| AU | 201224431311/2012 | 11/2012 |
| CN | 2376870 | 5/2000 |
| JP | 58-18802612/1983 | 12/1983 |

OTHER PUBLICATIONS 2021-560442 Japanese Application Translation of Official Action.
(Continued)

*Primary Examiner* — Aaron F Roane
(74) *Attorney, Agent, or Firm* — Neil D. Gershon

(57) ABSTRACT

A vibrating hand held surgical instrument for loosening tissue of a patient for liposuction or body contouring procedures. The instrument includes a motor connected to a vibration actuator having an eccentric rotating mass and an end effector for engaging tissue operatively connected to the vibration actuator, wherein the motor rotates the eccentric mass to cause the end effector to vibrate to loosen tissue. A flexible shaft having first end and second ends dampen the vibration to the motor and to the operator handle.

20 Claims, 14 Drawing Sheets

Related U.S. Application Data

No. 16/841,897, filed on Apr. 7, 2020, now Pat. No. 11,672,557.

(60) Provisional application No. 62/832,281, filed on Apr. 10, 2019.

(51) Int. Cl.
*A61N 7/02* (2006.01)
*A61B 17/00* (2006.01)
*A61B 18/00* (2006.01)

(52) U.S. Cl.
CPC ............... *A61M 1/76* (2021.05); *A61M 1/84* (2021.05); *A61M 1/89* (2021.05); *A61N 7/02* (2013.01); *A61B 2017/00398* (2013.01); *A61B 2017/00792* (2013.01); *A61B 2017/320028* (2013.01); *A61B 2017/32007* (2017.08); *A61B 2017/320084* (2013.01); *A61B 2017/320088* (2013.01); *A61B 2018/0019* (2013.01); *A61B 2018/00464* (2013.01); *A61B 2217/005* (2013.01); *A61B 2217/007* (2013.01); *A61M 1/77* (2021.05); *A61N 2007/025* (2013.01)

(58) Field of Classification Search
CPC  A61B 2017/00398; A61B 2017/00792; A61B 2017/320028; A61B 2017/320084; A61B 2017/320088; A61B 2018/0019; A61B 2018/00464; A61B 2217/005; A61B 2217/007; A61M 1/84; A61M 1/89; A61M 1/76; A61M 1/77; A61N 7/02; A61N 2007/025
USPC .......................................................... 604/22
See application file for complete search history.

(56) References Cited

U.S. PATENT DOCUMENTS

| | | | |
|---|---|---|---|
| 5,925,002 A | 7/1999 | Wollman | |
| 6,322,583 B1 | 11/2001 | Tu | |
| 8,066,691 B2 | 11/2011 | Khouri | |
| 8,167,830 B2 | 5/2012 | Noriega | |
| 9,457,177 B2 | 10/2016 | Dauvister et al. | |
| D796,671 S | 9/2017 | Khouri | |
| D801,523 S | 10/2017 | Khouri | |
| 2002/0151874 A1* | 10/2002 | Kolster | A61B 17/32002 604/542 |
| 2003/0187383 A1* | 10/2003 | Weber | A61M 1/89 604/22 |
| 2014/0257272 A1* | 9/2014 | Clark, III | A61B 17/32093 601/6 |
| 2015/0032143 A1 | 1/2015 | Khouri | |
| 2015/0216816 A1* | 8/2015 | O'Neil | A61B 18/02 514/738 |
| 2016/0375235 A1 | 12/2016 | Schoenle | |
| 2019/0099195 A1* | 4/2019 | Carroll | A61B 17/3476 |

OTHER PUBLICATIONS

European Search Report 207221482 Dated: Jun. 9, 2023.
PCT/US2020/027011 filed Apr. 7, 2020, International Search Report and Written Opinion dated Jun. 25, 2020.

* cited by examiner

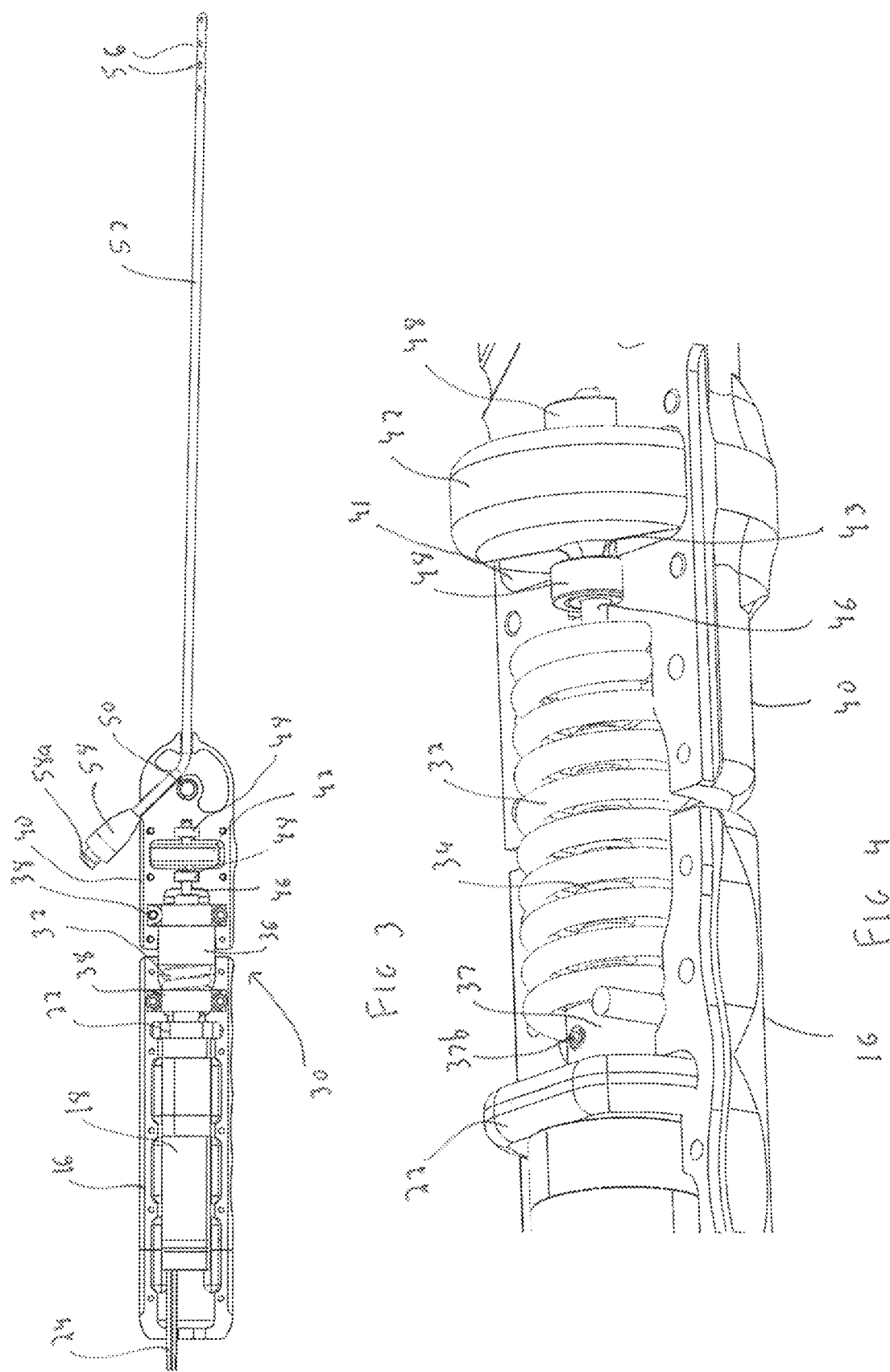

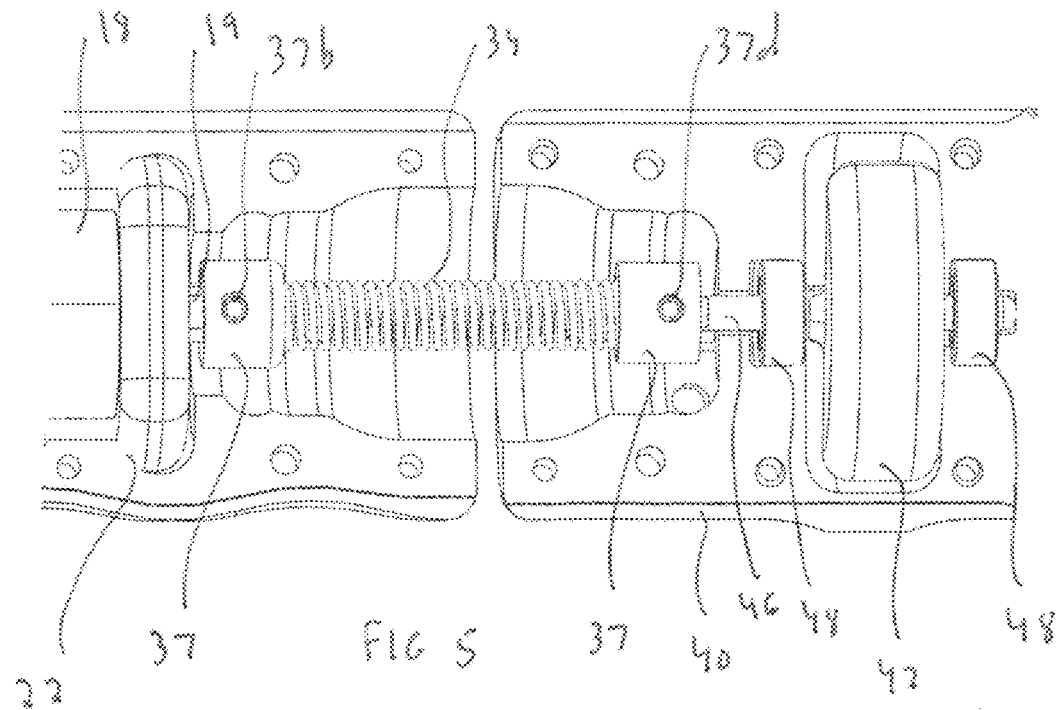
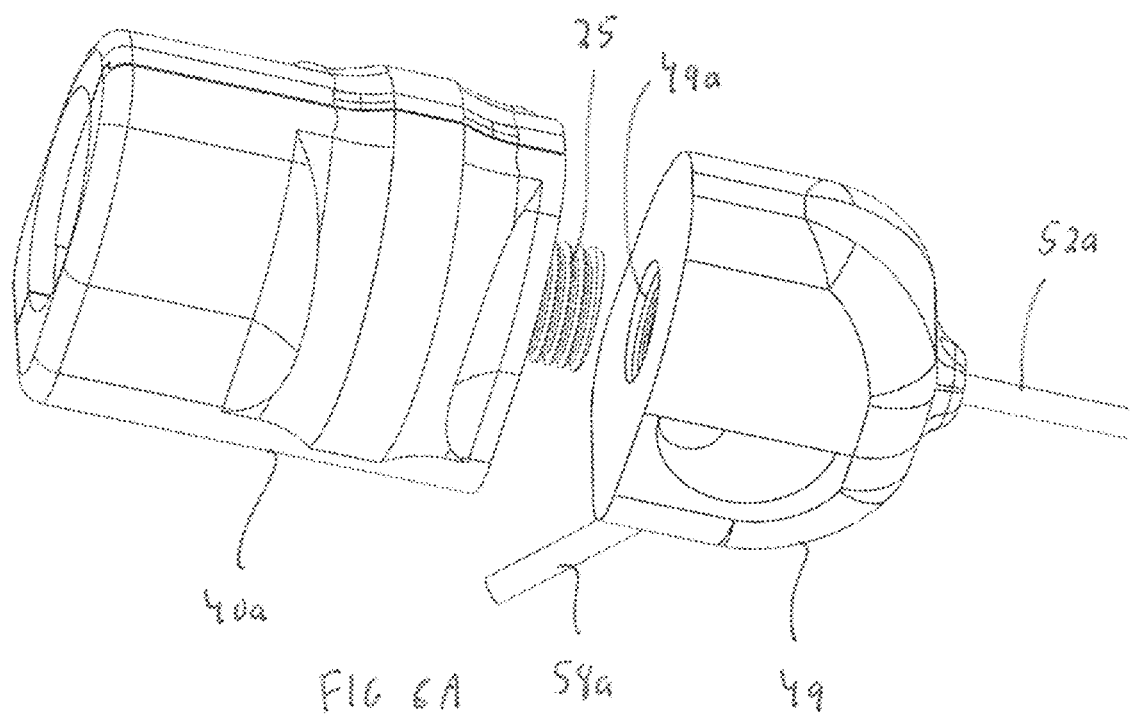

VIBRATING SURGICAL INSTRUMENT FOR LIPOSUCTION AND OTHER BODY CONTOURING APPLICATIONS

This application is a continuation of application Ser. No. 18/196,471, filed May 12, 2023, which is a continuation of application Ser. No. 16/841,897, filed Apr. 7, 2020, now U.S. U.S. Pat. No. 11,672,557, which claims priority to provisional application Ser. No. 62/832,281, filed Apr. 10, 2019. The entire contents of each of these applications are incorporated herein by reference.

BACKGROUND

Field of the Invention

The present invention is directed to a hand held vibrating device for liposuction and other body contouring surgical procedures.

Background

Liposuction is one of the most commonly performed surgical procedures. Liposuction is a procedure which slims and reshapes areas of the body for removing excess fat and improving body contours. Liposuction can be utilized for therapeutic reasons such as treating obesity or for cosmetic reasons to improve appearance. Liposuction is also frequently performed to harvest fat tissue that can be re-injected as autologous grafts to augment areas of volume deficiencies such as women's breasts after cancer resection. The procedure consists of making an incision, inserting a cannula into the space occupied by the fat tissue and suctioning the fat through the cannula that the surgeon's arm advances back and forth through the tissues. The procedure is often quite inefficient, requiring a significant amount of physical effort on the part of the surgeon, especially since to minimize the entry site incision and therefore the size of the resultant scar, the caliber (diameter) of the cannula is limited to 2-5 mm. This limits the entry site to few anatomical areas where the scar can be hidden and subsequently to the tissue region effected (loosened/broken up) by cannula movement. Another significant complication from such liposuction technique is unsightly surface contour irregularity that may result if the fat is unevenly harvested.

One of the existing techniques that is reported to reduce surgeon fatigue and help in the process uses a power-assisted liposuction device (PAL). An example of such device is disclosed in U.S. Pat. No. 5,911,700. The device adds to the surgeon's motion a 1-3 mm to-and-fro reciprocating motion of the cannula in the 40-90 Hz frequency range similar to that of a jackhammer. While this procedure is often referred to as vibration liposuction, the device does not truly vibrate but rather causes the cannula to reciprocate along the same linear (longitudinal) axis. The PAL technique reduces surgeon effort but the harvesting is still through the same linear channel ploughed by the cannula, thereby limiting the region effected by the device to essentially the cannula diameter.

Another device designed to help with liposuction is disclosed in U.S. Pat. No. 9,457,177 and claims to impart to the cannula a nutational motion that comprises a combination of a to-and-fro motion along with some vibration at the tip, depending upon the cannula length. However, the mechanism involved in this device does not directly induce vibration but instead, by using sudden hammer-like strikes of a piston moving back and forth inside a channel, delivers to the cannula some vibration effect in addition to the alternating back-and-forth movement.

Another device also designed to help with liposuction (Vibrasat®, Moeller Medical) imparts to the cannula an arcuate pendulum like motion to supposedly help loosen the tissues and harvest more efficiently. This is considered by some as an improvement over the PAL because in addition to harvesting out of the same ploughed tunnel like the reciprocating PAL, the sweeping motion harvests along an additional linear transverse path.

It is desirable to limit the size of the incision for liposuction for cosmetic reasons as well as reducing tissue trauma and patient recovery time. However, with such small incision, the foregoing devices are limited in their range of tissue harvesting. Therefore, it would be advantageous to increase the range of tissue harvesting without increasing the size of the incision.

Furthermore, the foregoing devices oftentimes create contour defects. It would be advantageous to provide a liposuction device that can better re-drape and help avoid the surface contour defect complications.

Low frequency vibration applied to biologic tissues can loosen their fibrovascular structural framework with less risk of damage than direct sudden strong striking force. A number of household items (e.g., toothbrushes, shavers, or the like) and industrial devices (e.g., vibrating tables, funnels, compactors, or the like) depend on vibration to reduce friction and to improve the flow, compaction, and/or diffusion of particulate matter, fluids, and/or air bubbles. Some medical devices also use low frequency vibration to prevent bone loss, to increase muscle mass, or to loosen mucus in the airways.

Vibration frequency can be in the infrasonic range (1-20 Hertz), sonic range (20-$10^4$ Hertz), ultrasonic range ($10^4$-$10^9$ Hertz), or the hypersonic range (>$10^9$ Hertz). A number of medical devices utilize ultrasonic vibration for diagnostic or for therapeutic applications. Some devices reported to facilitate liposuction utilize ultrasonic vibration at high frequencies. These high frequencies can cause tissue trauma and can be disadvantageous for body contouring procedures.

When autologous grafting is performed to augment the size or correct major body contour defects, such as micromastia, mastectomy, or lumpectomy deformities, filling the deficiency with graft tissue is not sufficient. Instead, the fibrous scar and any restrictive fibrovascular structural framework of the tissues should also be loosened to accommodate the additional volume. While using external expansion to prepare the recipient site to that effect such as disclosed in U.S. Pat. No. 8,066,691, and/or using devices that can percutaneously mesh expand the tissues to be enlarged, such as disclosed in U.S. Pat. Nos. D796,671 and D801,523 and U.S. Patent Publication 20150032143, the expansion is still limited.

It would be beneficial to improve the space for the graft and improve diffusion and flow of non-Newtonian fluids to facilitate the insertion and improve the dispersion of the graft particles (The Lipoaspirate is a Non-Newtonian fluid).

Vibrating handpieces can currently be found in novelty items commonly used for personal massage (e.g., U.S. Pat. Nos. 3,370,583 and 5,925,002). However, these handpieces are not designed to connect to surgical instruments and they lack the many features necessary for FDA approved surgical devices such as autoclave sterilizable, safe enough to be introduced inside patients, etc. Further, these handpieces are not designed to connect to liposuction cannulas and cannot effectively be used for liposuction or other body contouring surgical procedures.

A number of small electric devices use eccentric rotating masses (ERM) to produce desired vibrations. However, vibrators that have the ERM directly coupled to the electric rotating engine, such as alarm buzzers and small household items, are often limited in size and power. Larger, more powerful engines directly connected to ERM need very robust constructs (extra strong bearings, fasteners, dampeners, etc.) to protect them from vibratory wear and tear damage.

SUMMARY OF THE INVENTION

The present invention overcomes the problems and deficiencies of the prior art. The present invention provides a vibrating device that loosens or breaks up tissue at an optimized rate and frequency, thereby effectively striking the balance between avoiding tissue trauma and negatively impacting tissue integrity while providing surgical effectiveness. The devices of the present invention also break up/loosen tissue in a region larger than the cannula diameter without disadvantageously increasing the size of the surgical incision used to access the body cavity. This is achieved by the selected vibratory motion of the device, along with the accompanying drive system and vibration dampening system, while avoiding the disadvantages and deficiencies of electromechanical transducers that use alternating current and magnetic fields to cause a reciprocating movement of the cannula, back-and-forth motion of cannulas, that do not use harmonic or pure vibration, transverse arcuate oscillations and back-and-forth motion of a piston that generate both oscillations and head on impact terminal vibrations.

In accordance with one aspect of the present invention, a vibrating hand held surgical instrument for loosening tissue of a patient for liposuction or body contouring procedures is provided, the instrument comprising a motor and a rotating flexible shaft having a first end and a second end. The first end is operatively connected to the motor shaft. A vibration actuator includes an eccentric rotating mass operatively connected to the second end of the rotating flexible shaft. An end effector for engaging tissue is operatively connected to the vibration actuator, wherein the motor rotates the eccentric mass to cause the end effector to vibrate to loosen tissue.

In some embodiments, the end effector is permanently connected to the vibration actuator; in other embodiments, the end effector is removably mounted to the vibration actuator.

In some embodiments, the end effector comprises a cannula having at least one opening at a distal portion and a lumen for one or both of injecting fluid into the patient and/or aspirating tissue from the patient.

In some embodiments, the end effector is aligned with a longitudinal axis of the rotating shaft; in other embodiments the end effector is offset from the longitudinal axis of the rotating shaft.

In some embodiments, the instrument includes a dampening mechanism extending between the housing for the motor and the vibration actuator to dampen vibration of the end effector and connect the motor to the vibration actuator. In some embodiments, the dampening mechanism can include a first spring positioned over the shaft and a second static spring positioned over the first spring.

In some embodiments, a first coupler is connected at one end to a shaft of the motor and at the other end to a shaft on which the rotating eccentric mass rotates.

In some embodiments, a microcontroller is configured to selectively adjust at least one of a frequency or an amplitude of harmonic or pure (true) vibration of the vibration actuator.

In some embodiments, the microcontroller has a sensor and a servo control mechanism which receives information that allows it to tune the vibration of the device with the native vibration frequency of the treated tissues in order to reach or avoid resonance.

In some embodiments, the rotating eccentric mass imparts purely a vibratory motion to the end effector; in other embodiments, the rotating eccentric mass imparts reciprocal motion to the end effector in conjunction with the vibratory motion imparted to the end effector.

In accordance with another aspect of the present invention, a vibrating hand held surgical instrument for loosening tissue of a patient for liposuction or body contouring procedures is provided, the instrument comprising a cannula having a lumen for one or both of fluid injection into the patient or aspiration of tissue from the patient, a motor and a vibration actuator operatively connected to the motor, the motor actuating the vibration actuator to impart vibratory motion to the cannula so vibration is in multiple axes.

In some embodiments, the motor further imparts reciprocal motion to the cannula in conjunction with the vibratory motion.

In some embodiments, the cannula is removably mounted to the vibration actuator.

In some embodiments, the vibration actuator includes a shaft and a rotating eccentric mass mounted on the shaft. In some embodiments, the cannula is offset from a longitudinal axis of the shaft.

In some embodiments, the motor is directly coupled to the eccentric rotating mass in the vibration actuator and the dampening component protects the operator hand through a passive coil.

In some embodiments, the additional reciprocating motion is actuated by a separate solenoid mechanism connected to or interacting with the vibrating component.

In accordance with another aspect of the present invention, a method for performing loosening of soft tissue for liposuction or body contouring procedures is provided comprising: a) providing a hand held device having a motor, a vibration actuator operatively connected to the motor and a cannula operatively connected to the vibration actuator; and b) actuating the motor to effect rotation of the vibration actuator to effect vibration of the cannula in tissue, wherein an operator of the device is shielded from vibrations by a dampening mechanism connecting the motor to the vibration actuator.

In some embodiments, the method further comprises the step of extracting through the cannula fat dislodged from the soft tissue by vibrations. In some embodiments, the method further comprises the step of injecting fluids, therapeutic agents or a graft into the soft tissue during or after the vibrations.

In some embodiments, the method further comprises the step of inserting a rod or a tissue file to loosen the fibrovascular structural framework of the treated tissue and to also induce inflammatory reactions that can induce tissue shaping and remodeling.

In some embodiments, the method further comprises the step of selectively adjusting at least one of a frequency or an amplitude of the vibrations.

In some embodiments, the gripping portion around the motor has a dampening cover comprising rubber, foam, ribs, or other geometrical designed three dimensional structure that can further reduce transmission of the vibrations to the surgeon's hand.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIGS. 2 and 3 are side views of the device of FIG. 1 with a portion of the drive mechanism housing and the vibration actuator housing removed to show internal components;

FIG. 4 is an enlarged view of internal components of the device of FIG. 1 showing the springs of the dampening mechanism and the eccentric rotating mass of the vibration mechanism;

FIG. 5 is an enlarged view of internal components of the device of FIG. 1 with the static spring removed to show the flexible rotating shaft spring;

FIG. 6A is an enlarged perspective view showing a coupling of the end effector to the vibration actuator in accordance with an alternate embodiment of the present invention;

DETAILED DESCRIPTION OF PREFERRED EMBODIMENTS

Figure 1:
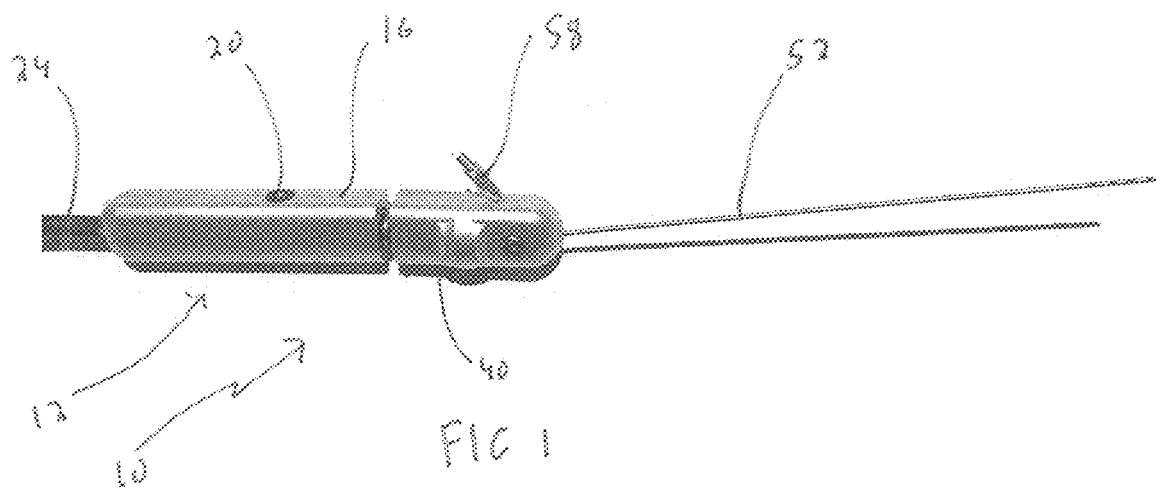
FIG. 1 is a perspective view of one embodiment of the device of the present invention.

The present invention provides a vibrating device (instrument) for performing surgical procedures such as liposuction, autologous grafting and other body contouring applications. The devices of the present invention in general include a handpiece/housing containing the motor for imparting vibration, a vibration mechanism/vibration actuator that produces the vibration, a dampening mechanism between the motor and vibration mechanism to dampen the vibration and an end effector attached to the vibration mechanism for engaging body tissue of the patient. Actuation of the motor rotates the motor shaft to thereby rotate the shaft supporting the vibration mechanism which rotates to effect vibration of the end effector, e.g., a cannula, to loosen or break up tissue. Various embodiments of these devices and their mechanisms/components are described in detail below. Note the terms "device" and "instrument" are used interchangeably herein.

In preferred embodiments, the end effector is in the form of a cannula and tissue is aspirated through a lumen of the cannula and/or fluid is injected through the lumen of the cannula. This is also discussed in detail below Various couplings to secure the end effector to the vibration actuator are described herein. In some embodiments, the end effector is non-removably (permanently) attached to the vibration actuator; in alternate embodiments, the end effector is removably attached to the vibration actuator. These various couplings are discussed in detail below.

In some embodiments, the end effector, e.g., cannula, is aligned with the longitudinal axis of the device. In alternate embodiments, the end effector is offset from the longitudinal axis, thus, in some versions, shortening the overall length of the device. These various embodiments are discussed in detail below.

The present invention provides a handheld device (instrument) that delivers to the end effector, e.g., cannula, a true harmonic vibration similar to the tip of a tuning fork. In doing so, the cannula tip covers a circular surface area much wider than the cannula and therefore potentially harvests fat out of a wider area. This allows the surgeon to harvest from a wide surface despite having a small cannula introduced through a concealed small puncture wound entry site. Stated another way, the same size incision can be used while providing a wider range of tissue harvesting. Furthermore, innocuous entry sites allow the surgeon if desired to use many sites which, with crisscrossing paths, that can suction more evenly and more effectively a particular anatomic area. By simultaneously covering a much wider footprint area, the effect in concept is similar to catching fish with a wide net compared to a spear. Furthermore, the vibration loosens the fibrous scaffold of the tissue, so they can better re-drape and help avoid the surface contour defect complications.

In preferred embodiments, the device uses low frequency true mechanical vibration in the $10$-$10^3$ Hertz range for liposuction and for additional reconstructive surgical procedures. In one embodiment, for example a harmonic vibrating handpiece may deliver this therapeutic vibration through one or more routes and at one or more intensity levels. Other ranges are also contemplated.

The low frequency mechanical vibration is advantageous for liposuction procedures which effectively loosen the tissue for removal by aspiration through the liposuction cannula.

For autologous grafting to augment the size or correct major body contour defects, such as micromastia, mastectomy, or lumpectomy deformities, the present provides for loosening the restrictive fibrovascular structural framework of the tissues to accommodate the additional volume. Augmenting the size improves the procedure since merely filling the deficiency with graft tissue is insufficient. This augmentation is achieved by the low frequency mechanical vibration of the devices disclosed herein which effectively loosen the structural framework to allow it to expand and make room for the grafts. Furthermore, the vibration improves the diffusion and flow of non-Newtonian fluids which facilitates the insertion and improves the dispersion of the graft particles (The Lipoaspirate is a Non-Newtonian fluid).

The lipoaspirate fluid obtained by liposuction contains a number of cell types in addition to the fat cells, or adipocytes. When lipoaspirate is used for fat grafting, it is believed that the active components responsible for the tissue augmentation are the stromal vascular fraction (SVF), or the adipose derived stem cells (ADSC) that mature into new fat, while most of the re-grafted adipocytes fail to revascularize and die. The vibration of the tissue during harvesting by the devices of the present invention loosens these small undifferentiated cells that typically accompany the capillaries and therefore result in collecting a larger proportion of these active components of fat transfer. This is akin to better shaking the tree to get more apples.

Furthermore, these low frequency mechanical vibrations of the devices disclosed herein loosen the structural framework while resulting in less damage to the vascular network than the percutaneous cutting and meshing techniques. In some embodiments, pure harmonic vibration, e.g., devoid of the back-and-forth jackhammering end strikes of the PAL and/or of the piston-based devices, can result in less trauma to the tissues, while still rendering them more plastic, deformable, and moldable. Accordingly, in preferred embodiments the surgical device delivers a true low frequency mechanical vibration. A pure or true vibratory motion as defined herein means vibration in multiple axes. The multiple axes are perpendicular or transverse to the longitudinal axis of the cannula. In reciprocal (back and forth) motion, the device moves along the longitudinal axis. In oscillatory motion, the vibration is in one axis, like a pendulum. In the pure vibratory motion of the present invention, the vibration is like a tuning fork or a piano string, vibrating along its length. The pure vibration occurs upon actuation and is not a result of impact as in reciprocal motion in which some vibration might occur when the tip impacts tissue.

Furthermore, in some embodiments, the system allows for control of the vibration amplitude and frequency and, thus, a physician may tune the same in order to resonate with the transducer device such as the cannula and the treated tissues. Similarly, depending on tissue resilience and toughness, some embodiments may provide a similar level of control over the frequency, amplitude and the strength of the vibration.

In some embodiments, the pure harmonic vibration of the devices disclosed herein may be delivered through a shield like transducer applied externally to the skin in order to loosen and to accelerate the diffusion of the injected fluids and the suspended particles. Additionally, or alternatively, the vibration may be delivered internally to deeper sites and multiple planes by inserting a solid rod like or file like dissecting probe to loosen the internal structural fibrous framework.

In some embodiments, the vibrating device may further include a liposuction cannula (as the end effector), whereby the vibration may facilitate the loosening of the fat lobules off their fibrous attachments and their capture by the cannula. Similarly, vibration of the cannula used for grafting may help disperse the graft, and without excessive trauma, loosen the restrictive structures in order to make room and accommodate for the graft. Still in other embodiments, the vibrating member can act as a tissue file or rasp to induce a controlled inflammation and injury that can result in scarring fibrosis and shrinking of the tissue envelope and help in lifting, rejuvenating, and remodeling various tissues such as the pendulous or misshaped breast. The foregoing are some examples of surgical uses as uses in other surgical procedures are also contemplated.

Experiment 1:

A scientific evaluation of the harvesting efficiency and the quality of the liposuctioned fat obtained with a vibrator hand piece connected to a liposuction cannula according to one embodiment (FIG. 1) of the present disclosure. This device was compared with the PAL (power assisted liposuction device) and performed liposuction on both sides of the same patient. In this experiment, the harmonic vibrating handpiece device was used on one side, and the PAL on the other side. Using a similar liposuction vacuum source and harvesting cannula on both devices, the amount of fat harvested over 12 minutes of liposuction was recorded and a sample tissue sent to a lab for stem cell analysis. It was found that liposuction with the harmonic vibrating hand piece was at least 30-45% more efficient than the PAL liposuction in terms of amount of fat harvested per minute of liposuction. Furthermore, there were about also 30-45% more SVF and ADSC per milliliter of liposuctioned fat in the sample collected with the harmonic vibrating handpiece than with the PAL.

This experiment evidences that vibrations produced according to embodiments of the present disclosure would loosen up the soft tissues and also cause more release of their mesenchymal stem cell contents. It also evidences that a vibrating cannula tip according to embodiments of the present disclosure would have a wider zone of harvest than a cannula pistonning back and forth in the same channel, resulting in greater efficiencies and harvesting more fat per stroke and per minute. Furthermore, on long term evaluation, the harmonic liposuction of the devices of the present invention using pure vibration resulted in better surface contour and more even tissue re-draping and shrinking than the PAL liposuction.

Various vibration frequencies and amplitudes were also found to have different effects that that may benefit different applications and requirements. For instance, larger amplitudes may be more efficient at lipoharvesting, but the use of larger amplitudes along with larger frequencies may cause too much trauma to delicate tissues and might be detrimental to the integrity of the recipient fibrovascular scaffold required for successful engraftment. The frequencies of the present invention achieve this optimal balance of efficiency and reduced trauma.

Furthermore, high frequencies, regardless of amplitude, may selectively harvest more adipose derived stem cells. Accordingly, some embodiments may be dynamic to adjust and tune the vibration frequency and corresponding amplitude depending upon the particular clinical requirements.

Referring now to the drawings and particular embodiments of the present disclosure, wherein like reference numerals identify similar structural features of the devices disclosed herein, there are illustrated several embodiments of the hand held surgical devices (instruments) of the present invention. With initial reference to FIGS. 1-3, the hand held device in accordance with one embodiment of the present invention is illustrated and designated by reference numeral 10. Device 10 includes a) a drive mechanism, also referred to as the drive system or engine system, containing the drive components; b) a vibration mechanism, also referred to as a vibration actuator, containing vibration components to effect vibratory motion; c) a dampening mechanism, also referred to as a dampening/connector system, containing the dampening components which dampens the vibration and also provides a connector mechanism for connecting the engine with the vibration actuator; d) an end effector, such as a cannula, which engages the patient's tissue and is operatively connected to the vibration actuator; and e) a clamping/connecting/component for operatively connecting the end effector to the vibration actuator. Each of the systems/mechanisms/components is discussed in detail below. Note as used herein, the term "connected" or "operatively connected" means either direct connection of the components or indirect connection where components are interposed between the two components but the two components are nevertheless joined/connected to interact.

In use, actuation of motor 18 causes rotation of eccentric rotating mass 42 via rotation of the flexible shaft 34. This causes vibration of the cannula 52 to loosen tissue. Tissue can be aspirated through the lumen in the cannula 52 during the procedure via one or more openings in the distal region of the cannula communicating with the lumen. The device 10 (as well as the other devices disclosed herein) can be used for liposuction, autologous grafting, body contouring procedures or for other surgical procedures where loosening tissue or breaking up tissue to re-structure their shape via the vibratory motion of the devices is beneficial.

Figure 2:
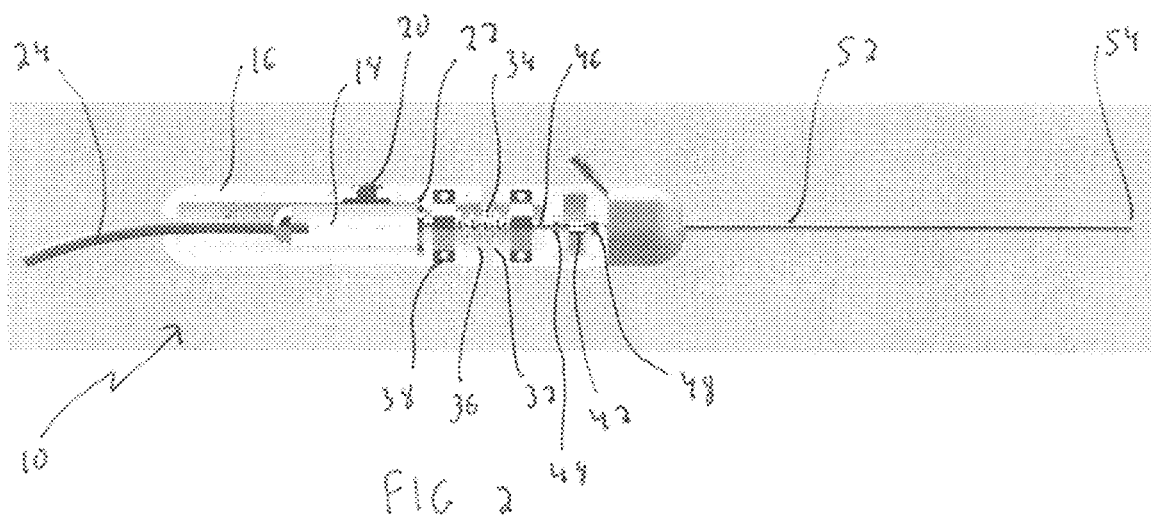

Turning first to the drive system, the system (engine components) includes a motor 18 contained in drive system housing 16. The drive system housing 16 also functions as the "handpiece" which the clinician holds during the surgical procedure, thus providing a handheld device. The motor can be an electric motor or, alternatively, a pneumatic rotating motor with the engine converting the hydraulic pressure into a rotational motion. In the embodiment of FIGS. 1-3, the motor illustrated is a brushless motor by way of example. The engine components further include a power source such as a battery (which in some embodiments can be sterilizable) which is enclosed in the housing 16 or alternatively a plug for connection to an external power source. In the embodiment of FIGS. 1-3, a cable 24 is connected to an external power source/controller. The engine component can further include various gauges, sensors, control mechanisms and switches for the motor.

Additionally or alternatively to a battery, the electric engine can use a power controller in the hand piece with electric wiring delivering the power and the feedback electric circuitry to the transformer or control module. In such embodiments, the power regulator may be located outside the surgical field. Such embodiments may allow for the display of the vibration frequency (e.g., correlated to engine rpm).

The drive system (motor) in some embodiments can be actuated by use of a foot switch for the operating surgeon. Additionally or alternatively, a manual control on the handpiece can activate the drive system.

The handpiece is ergonomically designed to comfortably fit in the surgeon's hand. It can be covered with a dampening rubber with ribs or cushions to reduce transmission of the vibrations to the surgeon's hand during use.

With continued reference to the embodiment of FIGS. 1-3, a manual control 20, accessible to the clinician, is positioned on housing 16. The control 20 can be in the form of a lever, button, etc. for actuation by the surgeon to activate the motor for rotation of the motor shaft to effect vibration as described below. A motor plate 22 adjacent a distal region of the motor 18 secures the motor 18 within housing 16 and protects it from having to bear the forces required to drive the effector through the tissues. Cable 24, which can have a pin connection as shown, extends proximally through an opening in the housing 16 and connects the motor 18 to an external power source or controller (not shown).

Note as used herein, the term "proximal" refers to the portion/region/component closer to the user and the term "distal" refers to the portion/region/component further from the user during use.

Further note the term "about" as used herein means±(plus or minus) 15% of the numeric value provided.

Cylindrical housing 40 is positioned distal of drive system housing 16 and spaced slightly distally axially therefrom. In the illustrated embodiment, the housing 40 has the same outer diameter as the cylindrical housing 16, although it could have a larger or smaller diameter. The cylindrical housing contains the vibration actuator. More specifically, positioned within vibration housing 40 is a motorized eccentric rotating mass (ERM) 42 that mechanically generates a pure vibratory effect (e.g., harmonic vibrations) without pistons moving back-and-forth and without the more complex piezo-electric electromechanical transducers that use alternating current to cause the oscillatory motion. The vibration amplitude of such a construct is a function of the mass and its eccentricity, while the frequency is a driven harmonic vibration of the cannula if the system is forced to vibrate at the frequency of the excitation or the rpm speed of the rotary engine.

Figure 10:
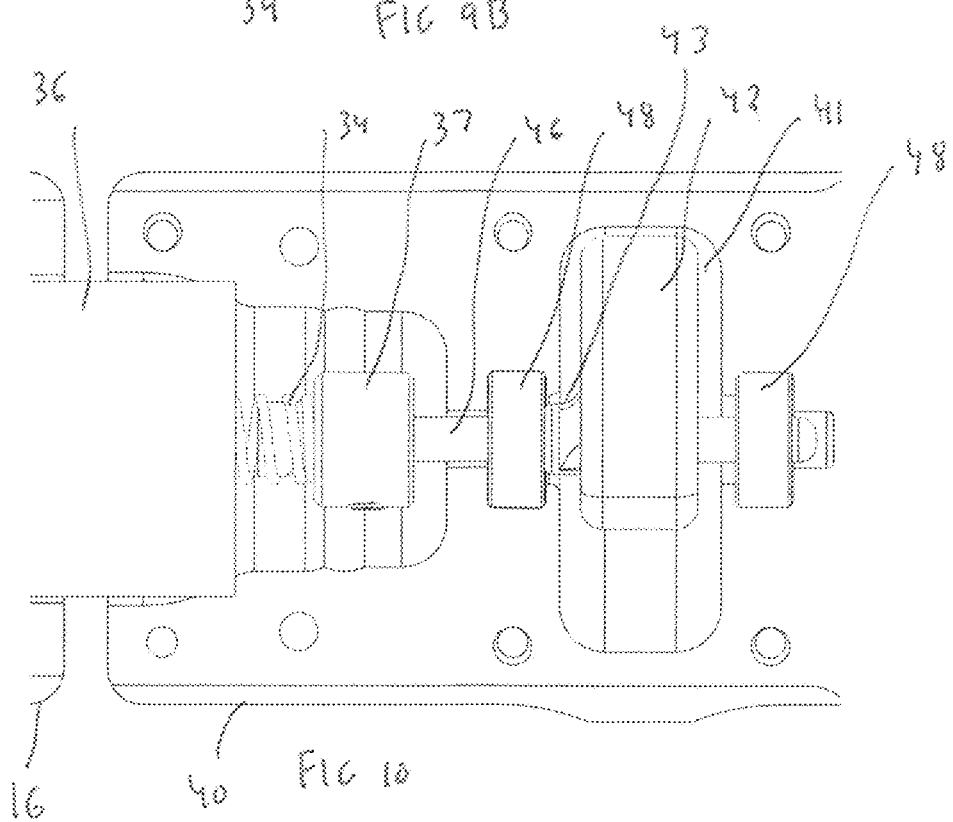
FIG. 10 is an enlarged view showing the eccentric rotating mass and roller bearings of the device of FIG. 1.

Eccentric mass (eccentric weight) 42 is connected to drive shaft 46 and is hemi-disc shaped, rotatable in cavity (channel) 41 (see FIGS. 4 and 10) and has an ear 43 (FIG. 10) that fits inside a groove in housing 40 that keeps the eccentric rotating mass 42 centered in the channel. Rotation of the eccentric mass 42 effects pure vibratory motion which is transmitted to the end effector. The position and eccentricity of the mass may be adjusted to vary the amplitude of the vibration.

The eccentric rotating mass 42 produces the vibration. The axis of the mass 42 can be held firmly between specially designed robust roller bearings 48, on the distal and proximal sides of the rotating mass 42, configured to withstand the lateral stresses, the axial loading forces, and the vibration.

The spring rotating shaft 34 (described in detail below) is slightly under tension to keep the ear 43 against the track of the bearing 48 to protect it. Spring rotating shaft 34 is connected to the rotating mass 42 through the connector as described below.

In some embodiments, the eccentric rotating mass 42 weighs about 10 grams to about 25 grams, the distance from the axis of rotation to the centroid is about 5 mm to about 25 mm and the outer diameter is about 2 cm to 6 cm. Note these values are given by way of example as other weights, distances and diameters (outside these ranges) are also contemplated as long as they achieve the function and benefits of the eccentric rotating mass 42 of the present invention. The mass 42 is sized so as not to exceed a size where the vibrating is too wide and impractical for surgery. On the other hand, it is sufficiently sized to effect the loosening or breaking up a sufficient area of tissue by the end effector, e.g., cannula. Note the foregoing dimensions were found to strike the optimal balance between, on one hand, too powerful vibrations which were found to be potentially damaging, and on the other hand, too weak vibrations which had minimal therapeutic effect.

The vibrator though needs to be of sufficient size and power. Larger and more powerful vibratory forces, which can be used in some embodiments of the present disclosure, may use more powerful engine torque in order to rotate a larger mass with significant eccentricity. Direct coupling of a powerful engine small enough to be hand held to a larger eccentric rotating mass, however, could cause excessive wear and tear and prohibitively premature fatigue failure of the electric engine component parts. Furthermore, it is advantageous to shield the operator's hand from these strong vibrations and wrapping the device with a dampening material while helpful, may not be sufficient. Another factor to be taken into consideration is the significant to and fro force required to advance the cannula through the tissues.

Shielding the engine from these compressive and distractive forces adds to the longevity of the device. To that effect, some embodiments of the present disclosure include a dampening connector to shield the rotating engine and the operator's hand from the strong vibrations of the eccentric rotating mass.

This dampening system/component can include a medical grade stainless steel flexible rotating shaft connected to the engine (motor) shaft on one end and on the other end to the shaft 46 of the eccentric rotating mass 42 located in the vibration actuator housing 40, The flexible rotating shaft is preferably spring-like and slightly tensed. While the flexible rotating shaft transmits the rotatory connection from the engine, a static but flexible static connecting shaft is provided to surround the rotating shaft to counteract the rotation and prevent the rest of the device from spinning. In device 10, the static connecting shaft is in the form of a spring. Alternatively, instead of a single spring design, this static connector may consist of a number of springs or bumpers arranged in an array all around the rotating shaft such that they prevent counter-rotation, maintain lateral flexibility, and dampen the vibration. For example, the static connection may comprise a spring or other flexible hollow structure, such as a rubber hose, that may enclose the rotating shaft and provide a dampening link between the hand piece component and the vibrating actuator component. This dampening connector component may preserve engine longevity and protect the surgeon's hand from excessive vibration.

An additional rubber connector can be provided to envelop the rotating shaft and the static connector and acts as a protective sealing component. An insulator component shields the patient from any accidental electric shock transmission. The electric insulation might be at multiple levels/locations but preferably at the clamping/connecting component or at the effector component.

The dampening connector may comprise a flexible rotating shaft to transmit the rotational motion to the eccentric rotating mass of the device with a flexible static connector wrapped around this shaft to mechanically link the engine/hand piece component to the eccentric rotating mass. This construct isolates the engine/hand piece component of the device from the vibrations of the eccentric rotating mass. Furthermore, to protect from the compressive and distracting forces of liposuction, the flexible rotating shaft transmitting the rotating motion is preferably pre-tensioned to a certain extent compared to the flexible static connector that is stiffer and not connected to the motor.

Turning now to FIGS. 4-5, the dampening mechanism (also referred to as the dampening connector system or components) of the device 10 of FIG. 1 is shown in more detail to provide one example of the aforedescribed dampening mechanism having a rotating and static connector. The dampening system includes a rotating shaft spring 34 which connects the shaft of motor 18 to the shaft 46 of the eccentric rotating mass 42. Spring 34 transmits the rotary connection to the engine so rotation of the motor shaft effects rotation of the eccentric mass shaft. A large spring 32 is positioned over, radially spaced from, the smaller rotating shaft spring 34 and provides the static connector to counteract rotation. The spring is slightly under tension to keep the ear 43 of the eccentric rotating mass 42 against the track of the bearing 48 as mentioned above. The spring constant of the static spring 32 is preferably about 50 lb/in to about 350 lb/in. It has been found that about 30 lbs force is required to prevent the vibrating head (housing 40) from hitting the handpiece (housing 16). That is, less force will cause it to hit and higher force will not allow for sufficient dampening. Therefore, the spring force of the device 10 is designed to achieve the optimal balance.

A rubber foam 36 (FIG. 3) and/or viscoelastic element can be used as sleeve over the spring, molded around the spring, and/or as couplings between the spring and device housings. This will increase the effective spring constant, provide further dampening and act as a seal. As shown in FIG. 3, the rubber foam connector 36 covers the shaft and seals the connection between the handpiece and the vibration actuator.

The rotating shaft spring 34 is flexible and collapsible, and is tensioned to shield the engine from the driving load. The spring 34 in the resting position of the device is extended about 2 mm to about 10 mm. Less extension can cause the spring shaft to buckle if the vibrating head and handpiece touch each other, while a greater extension leads to a high load on the motor and bearing and can cause the spring 34 to buckle. Its spring constant is about 2/1b/in ±(plus or minus) 0.5 lb.in. Higher can create damaging loads to the motor and bearings and lower can cause the shaft to fail.

Figure 9A:
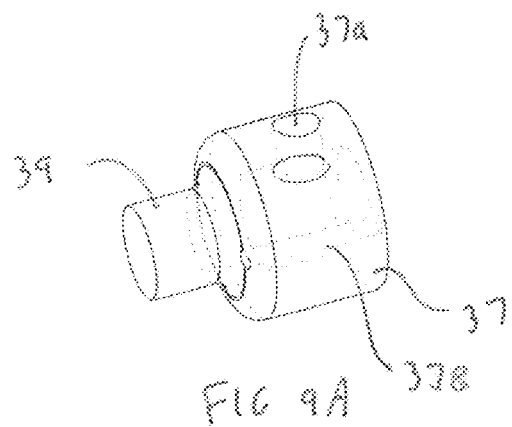
FIG. 9A is an enlarged perspective view of the connector of the device of FIG. 1 for connecting the motor shaft and the eccentric rotating mass shaft.
Figure 9B:
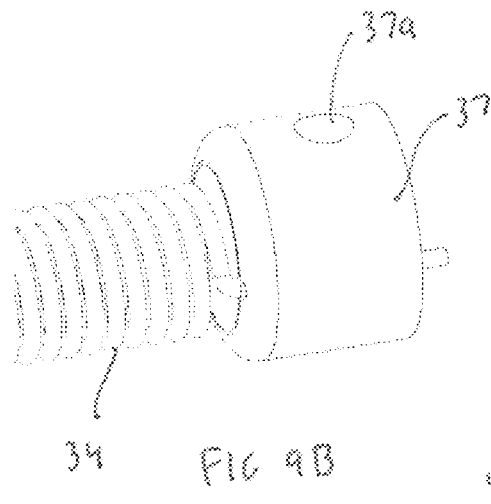
FIG. 9B is a view similar to FIG. 9A showing attachment of the rotating shaft spring to the spring extension of the connector.

The rotating shaft spring 34 is connected at opposing ends to connectors 37 as shown in FIGS. 5, 9A and 9B. The proximal connector (coupling element) 37 has a threaded hole 37a to receive a set screw 37b for securement of the proximal connector 37 that locks it into the motor shaft 19 and the distal connector (coupling element 37) has a threaded hole 37a to receive a set screw 37d for securement of the distal connector 37 that locks into the eccentric rotating mass shaft 46. Distal connector 37 has a proximally extending shaft extension 39 the fits on the inner diameter at a first end of the spring shaft 34. A groove 37e in connector 37 locks the tail of the coil spring. The distal connector 37 is shown in FIG. 9B with the spring 34 positioned over the connector extension 39. The extension of the proximal connector 37 extends distally to fit on the inner diameter of the shaft 34 at a second end of the spring shaft 34.

Clamping and/or connecting mechanisms are provided to connect the end effector to the vibrating actuator. The end effectors can be for example hockey stick bent liposuction cannulas, similarly configured lipografting cannulas, fluid infusion cannulas, rods, whether smooth or rough to act as tissue files, flat discs, etc. The cannulas can alternatively be L-shaped or T-shaped. Further the cannulas can be a single or multiple, e.g., double, lumen cannulas. The double lumen can provide, for example, fluid injection and aspiration through separate lumens so they can occur either separately or simultaneously.

In the embodiment of FIG. 1, the end effector 52 is in the form of a cannula having one or more side openings 56 (FIG. 3) at the distal region, and/or a distal opening at the terminal end of the lumen, for communication with the lumen extending therein. The cannula 52 is operatively connected (attached) to the vibration actuator so the vibration is transmitted to the cannula 52 to loosen tissue in liposuction, body contouring, or other surgical procedures. Cannula 52 is hockey stick shaped with angled connector 58 including a luer fitting 58a (or other form of attachment) connectable to a suction/injection source tubing for aspirating or for injecting for example saline to swell tissue, lipoaspirate, drugs or other fluids through the lumen and out the openings 56 of the cannula 52 into body tissue. Note other shapes of the cannula are also contemplated.

Various clamping and/or connecting (coupling) mechanisms to secure the end effector 52 to the vibration actuator component will now be described. In some embodiments, the end effector is permanently attached to the vibrator actuator such as in the embodiment of FIG. 1; in other embodiments, the end effector is removably/releasably attached to the vibrator actuator. The removable attachment enables use of different sizes or type of end effectors with the same handpiece. The coupling mechanisms may connect end effectors such as a shield like external skin vibrator, a rod like internal vibrator, a file-like internal rasp, a cannula for fluid infusion, liposuction or lipoinjection, etc. The end effector in the Figures is a cannula for aspiration/fluid injection for procedures such as liposuction, grafting and body contouring procedures, however, it should be understood that other end effectors can be used with the devices of the various embodiments disclosed herein.

In FIG. 1, the cannula can be permanently attached by connector clamping member 50 in housing 40 which applies a clamping force to the cannula at the region adjacent the bend or alternatively the cannula can be removably/interchangeably connected to the housing 40 with a bolt/nut screw mechanism such as shown in FIG. 8 as described below.

FIGS. 6A-8B show alternative embodiments of connectors for releasably attaching the end effector to the vibration actuator. However, it should be understood that these mechanisms could also be utilized for permanent attachment of the end effectors. Also, it should be understood that other mechanisms can be utilized to removably or non-removably attach the end effector to the vibration actuator.

With reference initially to the embodiment of FIG. 6A, the vibration housing 40a for the vibration actuator has a screw 25 extending distally therefrom which is inserted into proximal opening 49a of head or cap 49 of end effector 52a. Head 49 can be composed of plastic. This threaded engagement removably attaches the end effector 52a to the vibrator actuator. Note cannula 52a, with angled luer connector 58a is identical to cannula 52 of the embodiment of FIG. 1. Further, except for the attachment mechanism, the components of the device of FIG. 6A are identical to the components of the embodiment of FIG. 1 so for brevity further discussion is not warranted since the features and functions of device 10 are fully applicable to the embodiment of FIG. 6A, the difference being the removable threaded connection.

Note the cannula is shown as hockey shaped, however, as noted above, in the embodiments of FIGS. 1 and 6A-8B (and in other embodiments disclosed herein), the cannula can alternatively be L-shaped or T-shaped, and can be a single or multiple lumen cannula.

The cannula, if composed of metal, can have a plastic casing thereover to provide electrical isolation.

Figure 6B:
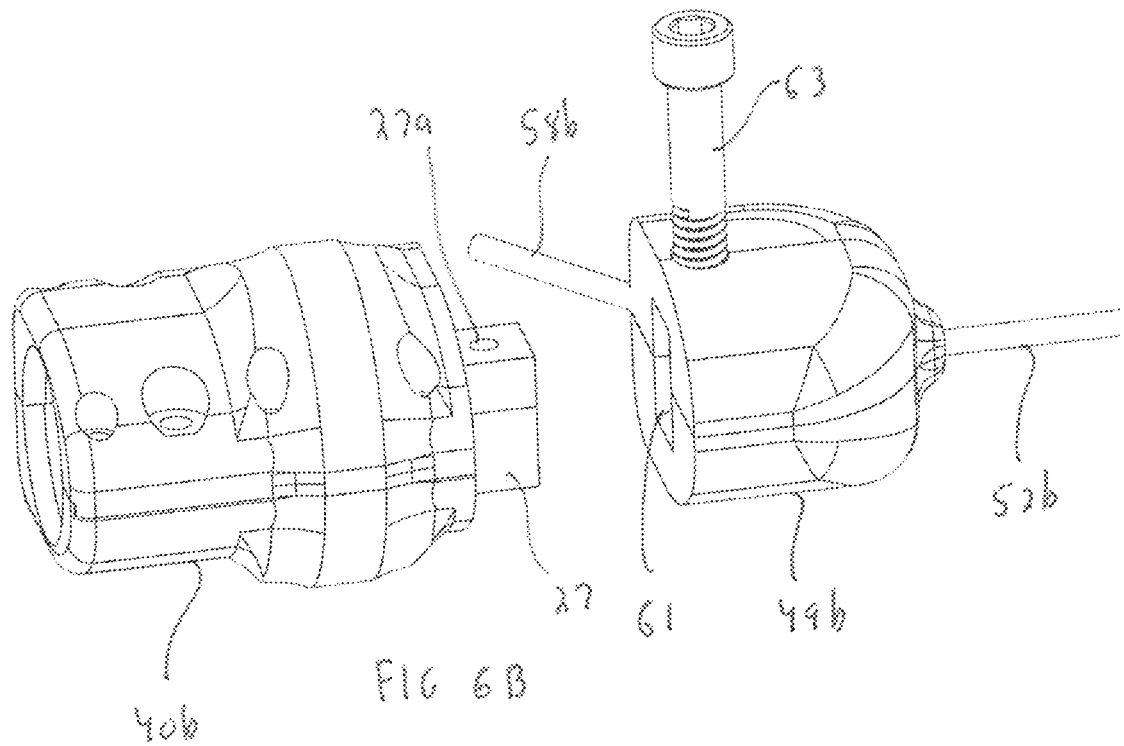
FIG. 6B is an enlarged perspective view similar to FIG. 6A showing an alternate embodiment of the coupling for the end effector and vibration actuator.
Figure 6C:
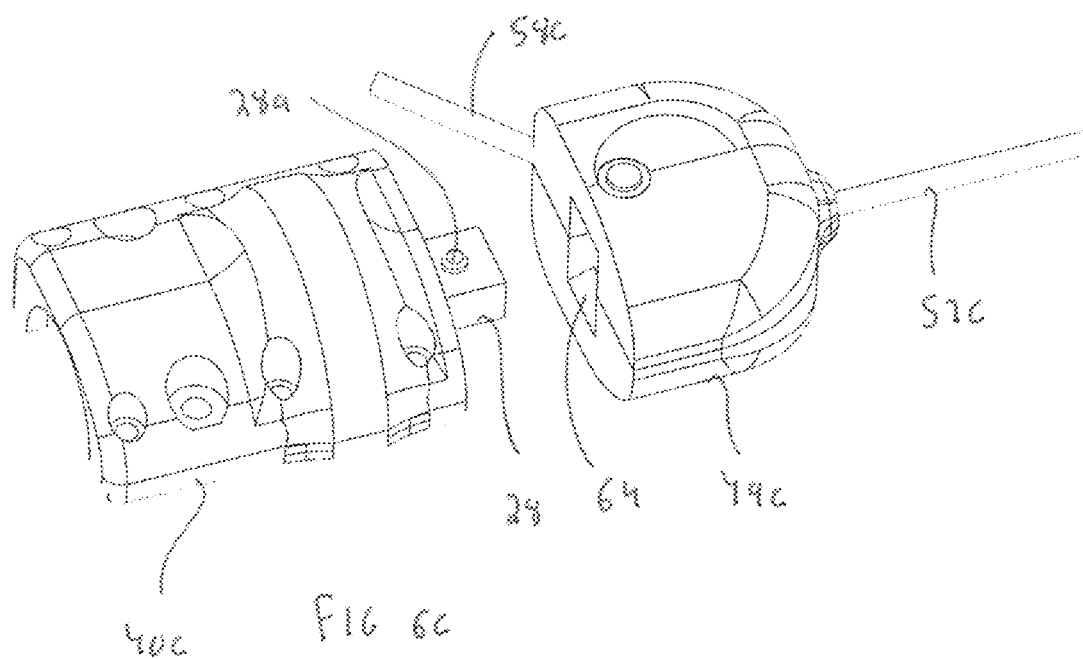
FIG. 6C is an enlarged perspective view similar to FIG. 6A showing another alternate embodiment of the coupling for the end effector and vibration actuator.

In the alternative embodiment of FIG. 6B, the housing 40b for the vibration actuator has a polygonal fitting 27 extending distally therefrom which is inserted into corresponding dimensioned proximal opening 61 of head or cap 49b of end effector 52b. Screw 63 extending through the opening in the cap 49a, transverse to the longitudinal axis of the device, extends through opening 27a in fitting 27 to secure these two components (cap 49b and housing 40b). Note cannula 52b has an angled luer connector 58b like cannula 52 of the embodiment of FIG. 1. In FIG. 6C, a pin lock secures end effector cap 49c to vibration housing 40c as it extends through opening 28a in polygonal fitting 28 which extends distally from vibration housing 40c and is insertable into corresponding dimensioned opening 64 in housing 49c of the end effector 52C. Note the fittings 27 and 28 can be shapes other than those shown. Note cannula 52c has an angled luer connector 58c like cannula 52 of the embodiment of FIG. 1. Further, except for the attachment mechanism, the components of the devices of FIGS. 6B and 6C are identical to those of FIG. 1 so for brevity further discussion is not warranted since the features and functions of device 10 are fully applicable to the embodiment of FIG. 6B and the embodiment of FIG. 6C.

In the alternative embodiments of FIGS. 7A-8B, a clamping mechanism removably/releasably secures the cannula to the vibration actuator. Note in FIGS. 6A-6C, the end effector is mounted via a cap or housing which is connected to the vibration actuator; in the embodiments of FIGS. 7A-8B the cannula itself (without a cap) is mounted to the vibration housing.

Figure 7A:
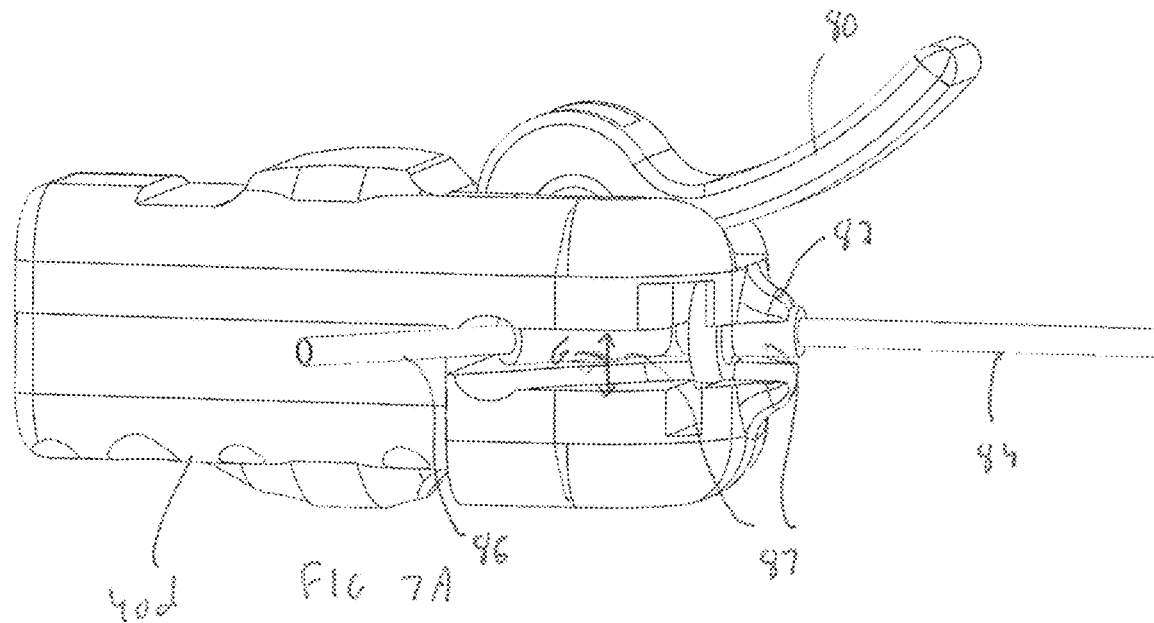
FIG. 7A is an enlarged perspective view of an alternate embodiment of a coupling for removable connection of the end effector to the vibration actuator, the clamp shown in the open position for attachment or release of the end effector.
Figure 7B:
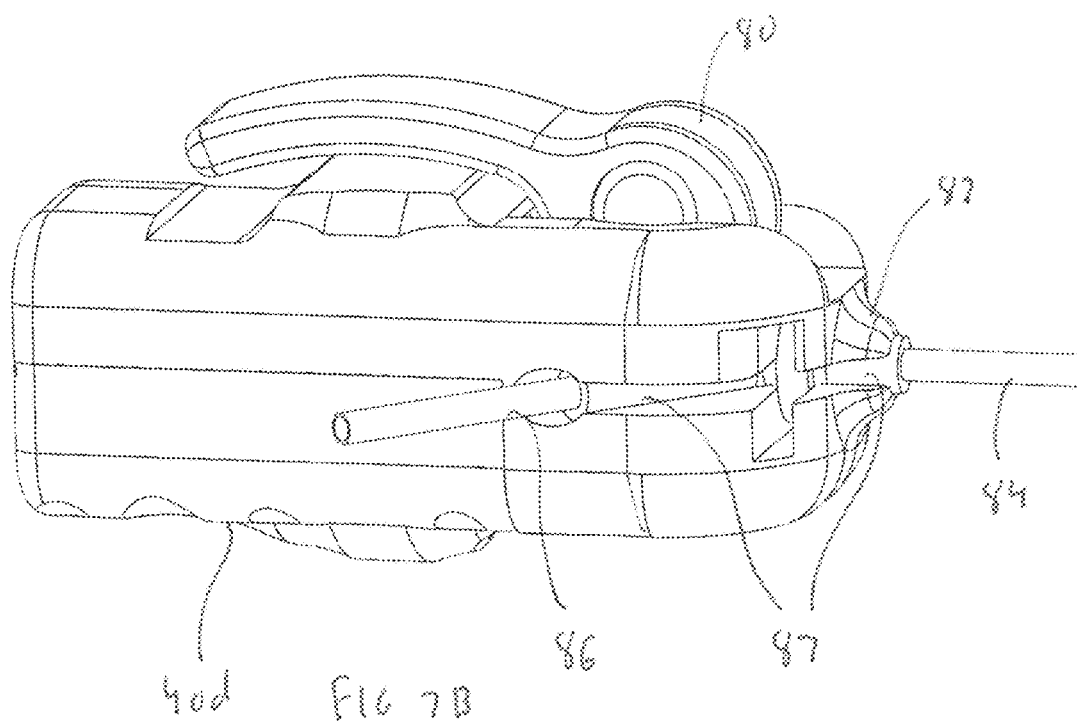
FIG. 7B is a view similar to FIG. 7A showing the clamp in the closed (clamping) position to secure the end effector to the vibration actuator.

Turning first to the embodiment of FIGS. 7A and 7B, cannula 84 has an angled luer connector 86 like cannula 52 of FIG. 1. A plastic sleeve 87 is placed over portions/regions of the cannula thereover to provide electrical insulation. The sleeve 87 can cover a part or the entire length of the cannula 84.

The proximal end of cannula 84 is inserted into the nipple or pointed tip 82 of the housing 40d for the vibrator actuator. The connector is shown in FIG. 7A in the unclamped (release) position. In this position, the nipple 82 provides a sufficient gap so the end effector can be removably received (mounted) therein. Angled portion 86 extends through a gap in the housing 40d as shown. Clamp lever 80 is in the open unclamped position. When it is desired to secure the cannula 84 once inserted into the nipple 82, lever 80 is moved (rotated) from the position of FIG. 7A to the clamping position of FIG. 7B. This forces the housing to close gap G and the spacing in the nipple 82 to clamp down on (grip) the cannula 84. The locked cam thereby holds the end effector tightly in place. If it is desired to release the cannula 84, the clamp lever 80 is returned to its position of FIG. 7A to open the gap/spacing so the cannula 84 can be slid out of the nipple 82 and gap in the housing 40d. Note the clamping force can be applied to the insulation sleeve 87 as shown in FIG. 7A, or in alternative embodiments, directly on the cannula 84.

Figure 8A:
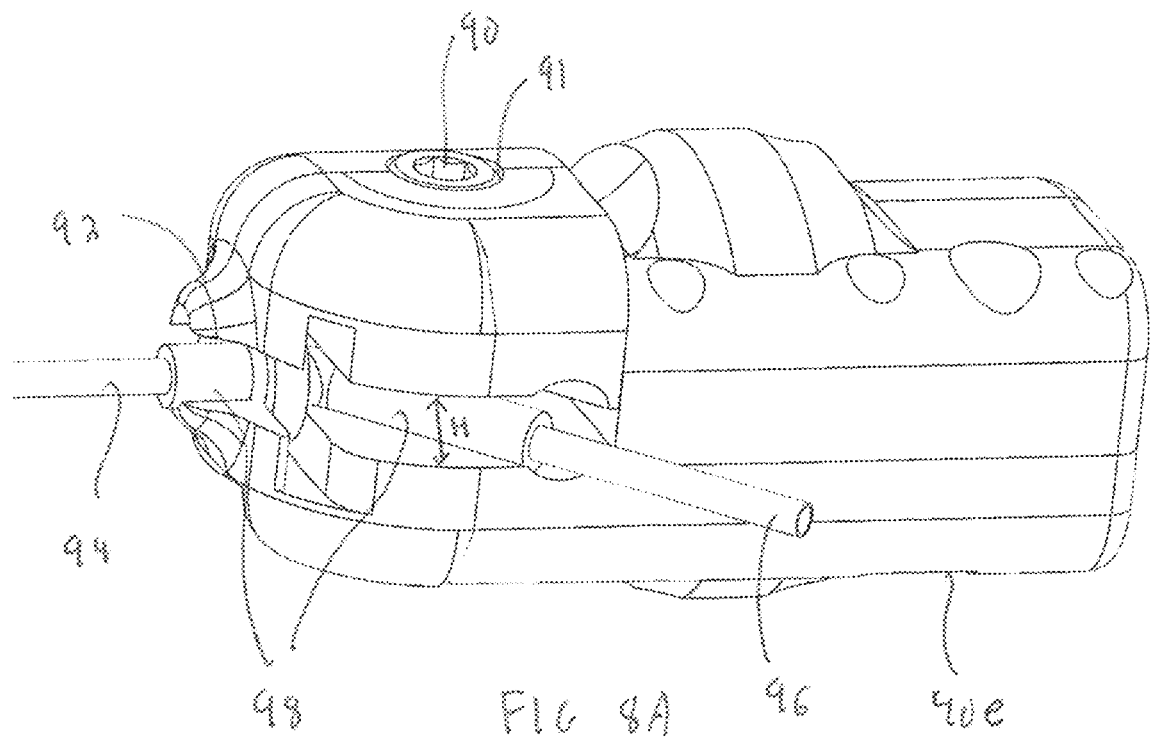
FIG. 8A is an enlarged perspective view of an alternate embodiment of a coupling for removable connection of the end effector to the vibrator actuator, the coupling shown in the position for attachment or release of the end effector.
Figure 8B:
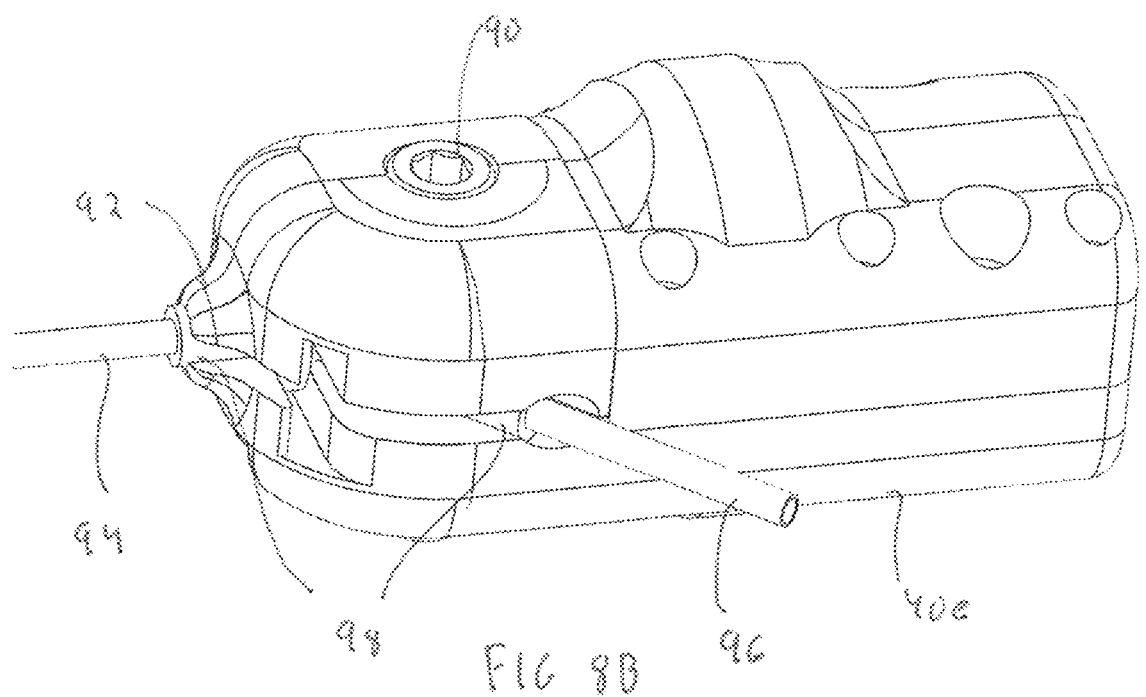
FIG. 8B is a view similar to FIG. 8A showing the end effector attached (secured) to the vibration actuator.

The embodiment of FIGS. 8A-8B is similar to the embodiment of FIG. 7A-7B except that instead of a clamp lever to clamp down on the plastic sleeve of the cannula, a threaded screw is utilized for coupling the vibration actuator to the end effector, e.g., cannula, as the tightened screw holds the cannula tightly in place. Screw 90 is inserted and tightened through the opening 91. This closes the gap H so the housing 40e and nipple 92 can clamp down on (grip) the cannula 94. The plastic sleeve 98 positioned over a portion of cannula 94 and angled luer connector 96 provides electrical insulation. The housing 40e clamps down on the insulation sleeve 98 as shown, but in alternative embodiments, can clamp directly on the cannula 94.

Note the plastic sleeve 87 (or 98) that is locked by the clasping mechanism can have the same outer design and caliber regardless of the caliber of the end effector utilized.

In the foregoing embodiments, the end effector, e.g., cannula, is aligned coaxial, and along the longitudinal axis of the device. The end effector, however, in alternate embodiments, can be offset from the longitudinal axis. This offset can be within the confines (diameter) of the handheld device; or, alternatively, outside the confines of the hand held device such as depicted in FIGS. 13A and 13B.

Figure 13A:
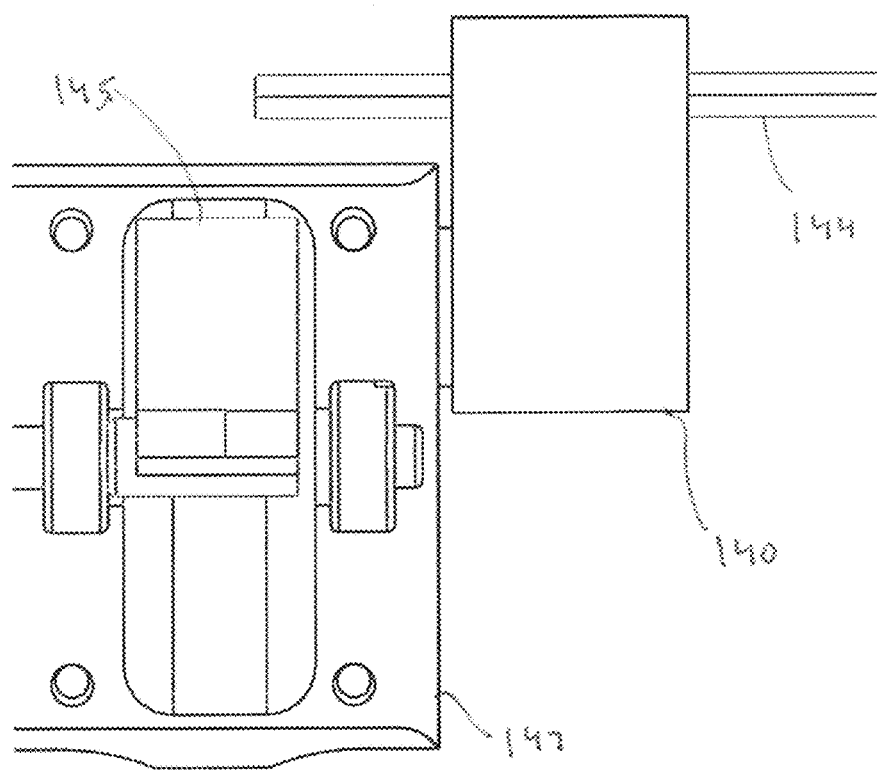
FIG. 13A is a side view of an alternate embodiment of the device of the present invention having an offset end effector.
Figure 13B:
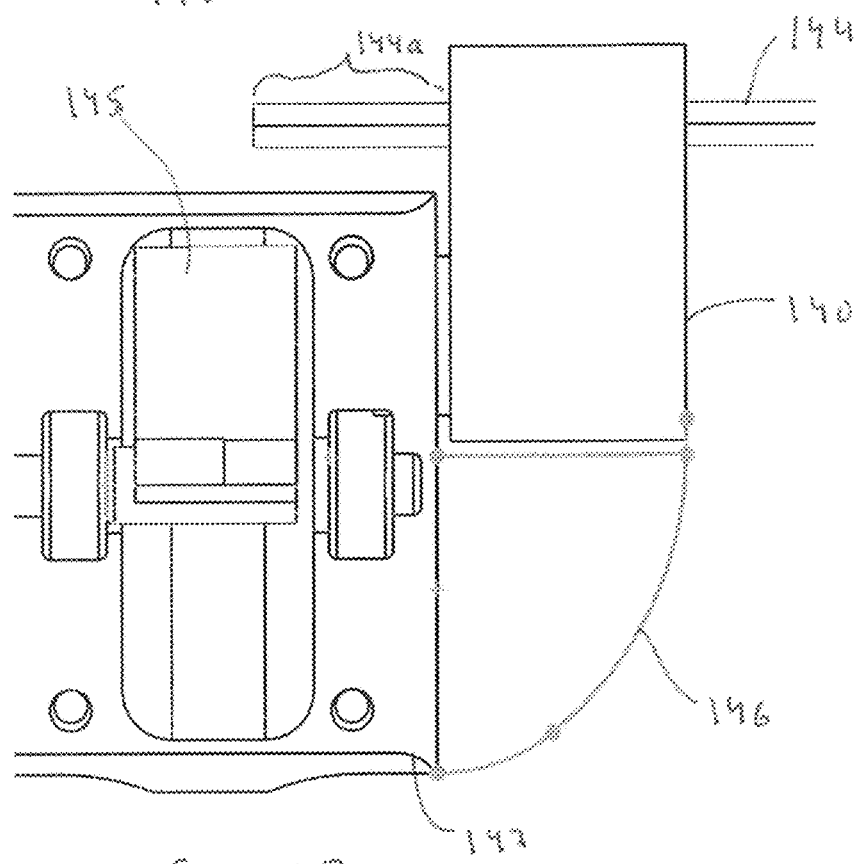
FIG. 13B is a side view of another alternate embodiment of the device of the present invention having an offset end effector.

In the embodiment of FIGS. 13A and 13B, a connecting component or connecting housing 140 is attached to the vibration actuator housing 142 (which contains the eccentric rotating mass 145 identical to rotating mass 42 and the roller bearings described above). The connection component 140 is offset from the housing 142 so the channel to receive the end effector, e.g., cannula, 144 is radially spaced from the longitudinal axis of the rotating shaft of the eccentric mass 145 and the motor shaft (not shown). In this manner, cannula 144 is radially offset from the longitudinal axis of the device. In FIG. 13B, the device includes an additional component 146 to round off the exposed edge of the vibration actuator 142. The cannula 144 can be permanently or removably connected to the housing 140. The removabilility can be provided by having the housing 140 permanently attached to housing 142 and removing the cannula from a channel in the housing 140 or alternatively having the housing 140 removably attached to the housing 142 with the cannula either removably or permanently secured in housing 140. Various connections can be used to attach the housing 140 and housing 142 such as clips, screws etc. as well as the attachments, e.g. fittings, utilized in FIGS. 6A-6C, for example.

Offsetting the cannula 144 (in this and the other offset cannula embodiments) and placing it along the side of the vibration actuator housing 142 has the advantage of shortening the overall length of the device, That is, in the embodiments wherein the cannula is aligned with the longitudinal axis, the proximal end of the cannula extends from the distal edge of the vibration actuator housing; in the offset embodiments, a region 144a of the cannula 144 is proximal of the distal edge, shortening the overall length of the device by the length of region 144a. The dampening mechanism, vibratory motion, etc. of the device of FIGS. 13A, 13B are otherwise the same as in device 10 so the features/components and functions of device 10 are fully applicable to the device of FIGS. 13A and 13B, e.g., eccentric rotating mass, bearings, dampening mechanism, motor etc.

Vibration and Reciprocation

In the foregoing embodiments, the end effector moved in purely vibratory motion via the rotating eccentric mass. In alternate embodiments, a reciprocal motion to the end effector is provided in conjunction with the vibrational motion. This helps to reduce the force required to be exerted by the surgeon as the surgeon pushes through tissue during the surgical procedure. Thus, in these embodiments, the vibration actuator induces a to and fro reciprocation in addition to the harmonic or pure (true) vibration.

Such motion can be achieved in some embodiments by interposing an additional piston/cylinder component that can slide back and forth over the vibration actuator component and connect to the clamping/connector component. The back and forth excursion of this reciprocating part could be actuated in some embodiments by a rod and cam mechanism that might be circular, disk-like or ovoid, while its motion is constrained by the piston/cylinder configuration and balanced by springs.

Figure 11A:
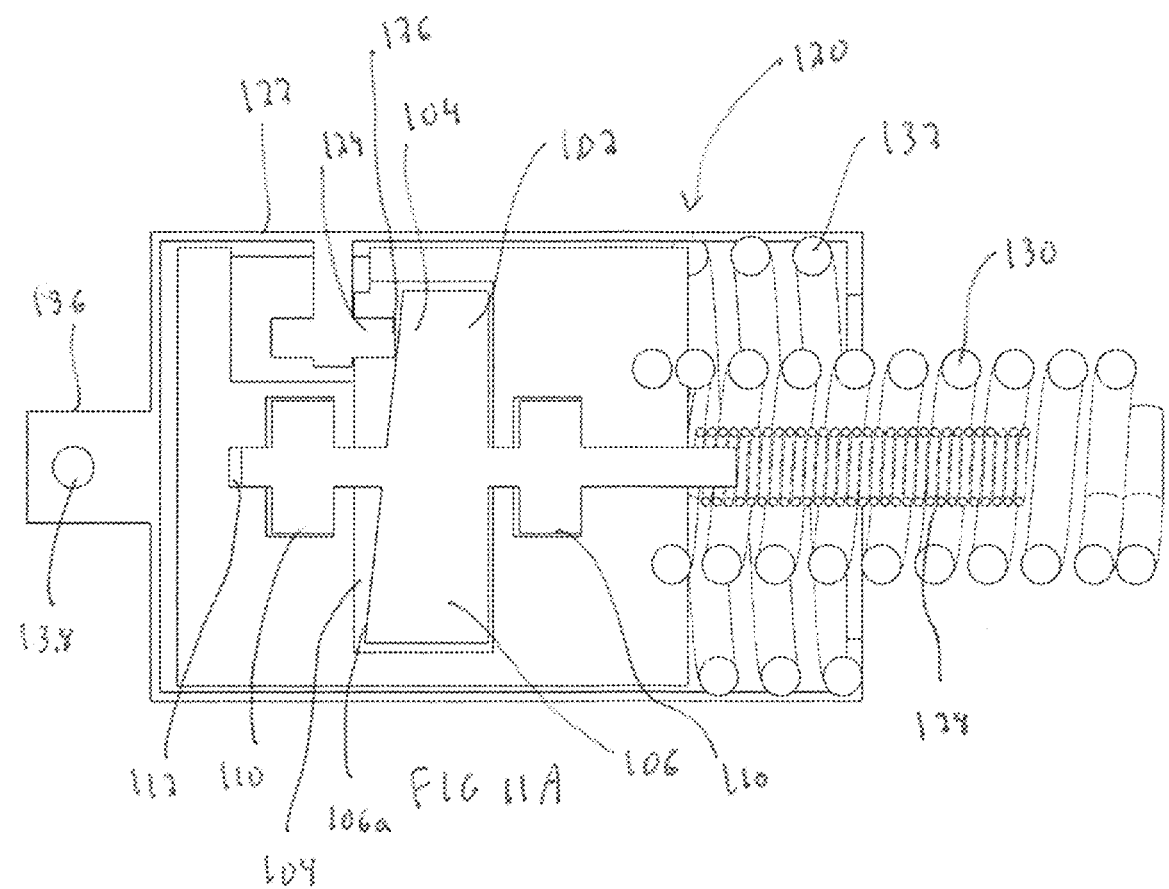
FIG. 11A is an enlarged side view showing an alternate embodiment wherein the eccentric rotating mass of the device imparts a vibratory and reciprocal motion, the eccentric rotating mass shown in the position wherein the sleeve and cannula are in the backward (proximal) position.
Figure 11B:
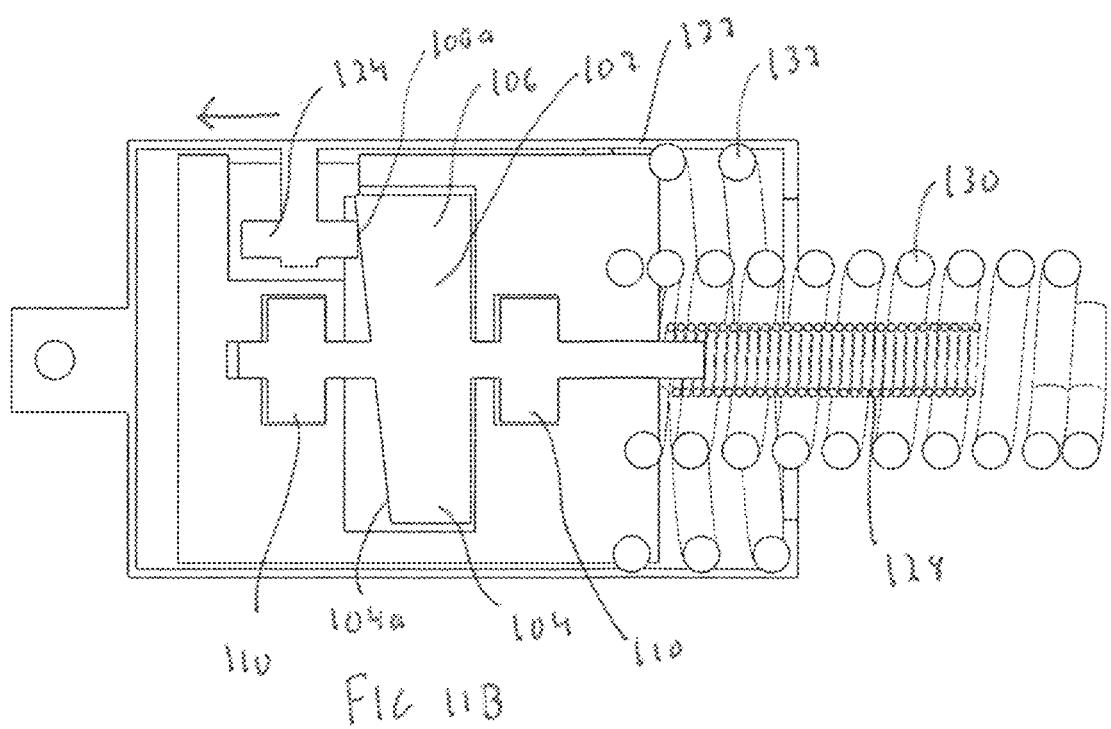
FIG. 11B is a view similar to FIG. 11A showing the eccentric rotating mass rotated to a second position wherein the sleeve and cannula are in the forward (distal) position.

An example of a rod and cam mechanism is shown in FIGS. 11A and 11B. Rotating eccentric mass 102 is asymmetric disc-shaped with one portion (region) 104 having a reduced width (transverse dimension), as compared to portion (region) 106 at the opposing end, to thereby provide a narrower portion. Outer sleeve 122 has a rod 124 extending inwardly therefrom having a surface or edge 126 engaged by the camming surface 106a of wider region 106. The outer cylinder (sleeve) 122 can have a restorative spring 132 to keep the bearings 110 in contact with the cam weight.

In the initial backward excursion (proximal) position of FIG. 11A, the surface 104a of narrower portion 104 is contiguous with or slightly spaced from edge 126 of rod 124, but no or minimal distal force is applied to the rod 126. When the eccentric rotating mass 102 rotates within cavity 108 of vibration actuator housing 120, camming surface 106a of wider portion 106 applies a force to surface 126 or rod 124 to move rod 124 and attached sleeve 122 in a distal direction (see arrow in FIG. 11B). When the eccentric rotating mass 102 is rotated back to the position of FIG. 11A, the narrow portion 104 is adjacent the rod 126 and thus the force against (camming of) rod 126 is removed. This enables the sleeve 122 to return to its proximal position. As can be appreciated, as the eccentric mass 102 rotates, the sleeve 122 is moved to and fro (back and forth) in a reciprocating motion in conjunction with the vibratory motion imparted to sleeve by the rotating eccentric mass 102 to thereby impart a vibratory and reciprocal motion to the end effector, e.g., cannula, attached to connector 136 via opening 138. Thus, in this embodiment, the eccentric rotating mass 102 which induces vibration similar to the hemi-disk of FIG. 1, also works as a cam for reciprocating the end effector. Stated another way, the disk-like eccentric cam 102 also functions as the eccentric rotating mass to induce the vibration of the end effector.

Note the device of FIGS. 11A and 11B is otherwise the same as device 10 of FIG. 1 and includes e.g. bearings 110 (like bearings 48), a dampening mechanism having a rotating shaft spring 128 (like rotating shaft spring 34), static connecting shaft large spring 130 (like static spring 32), a motor, etc.

Figure 12A:
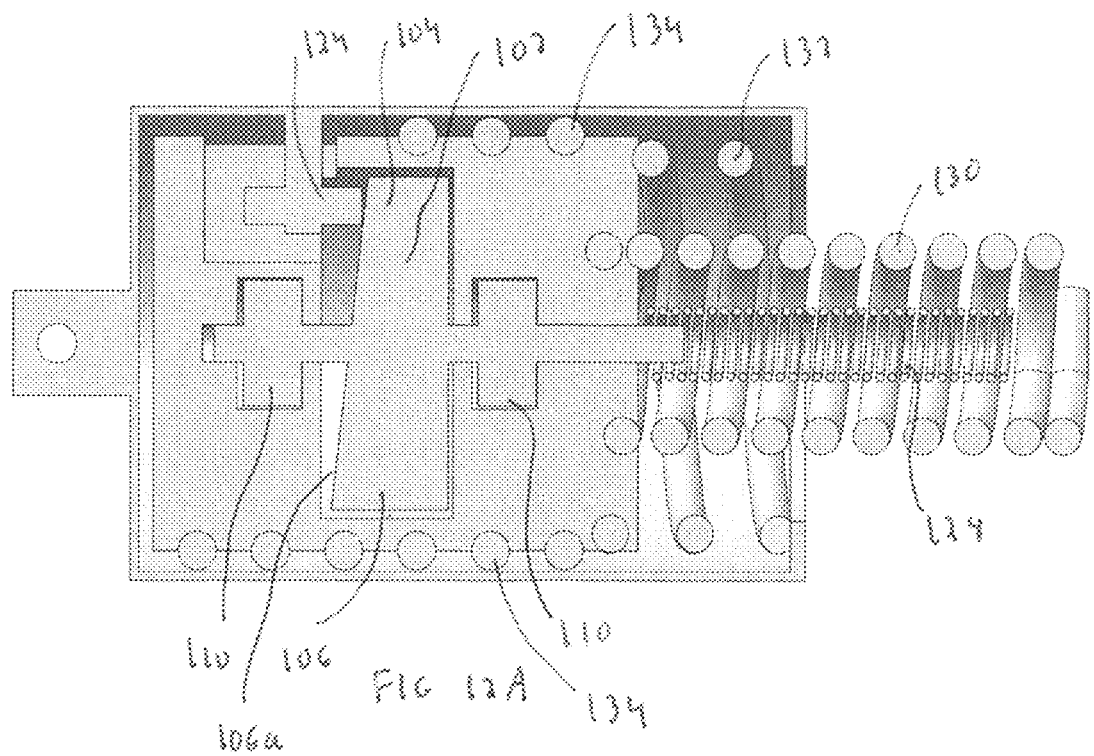
FIG. 12A is a view similar to FIG. 11A showing an alternate embodiment having ball bearings to reduce friction in the reciprocal movement of the outer sleeve.
Figure 12B:
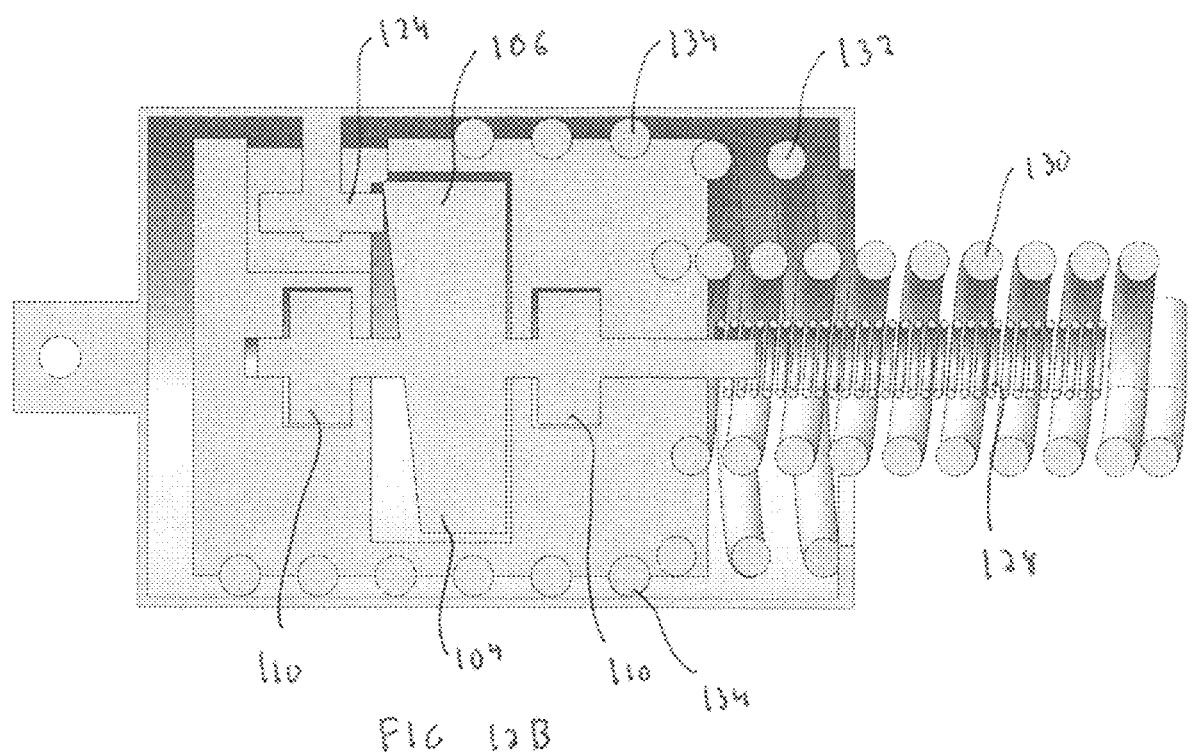
FIG. 12B is a view similar to FIG. 12A showing the rotating mass rotated to a second position wherein the sleeve and cannula are in the forward position.

The sleeve 122 could include ball bearings 134 as shown in the alternate embodiment of FIGS. 12A and 12B to reduce friction in the piston/cylinder reciprocating motion and improve longevity of the device. Otherwise, the embodiment of FIGS. 12A and 12B is identical to the embodiment of FIGS. 11A and 11B and is provided with the same reference numerals.

Note the sleeve with the rod could be an outer sleeve as shown or alternatively positioned within an outer sleeve.

Figure 14A:
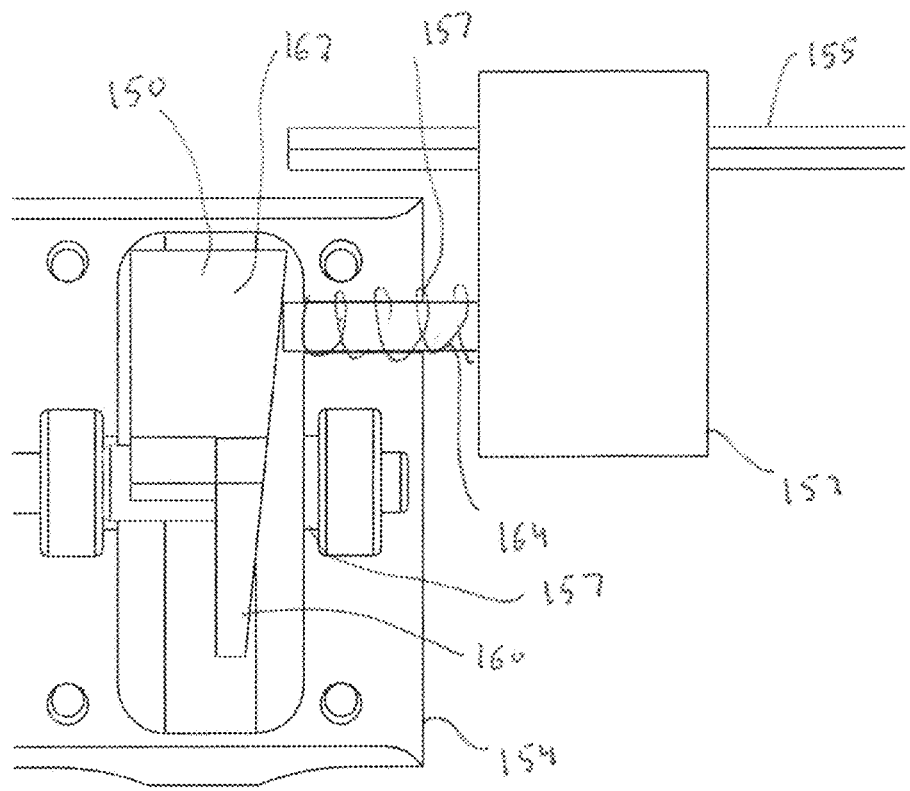
FIG. 14A is a side view of an alternate embodiment of the present invention having an offset end effector in a device that imparts a vibratory and reciprocal motion, the eccentric mass shown in the position wherein the cannula is in the forward (distal) position.
Figure 14B:
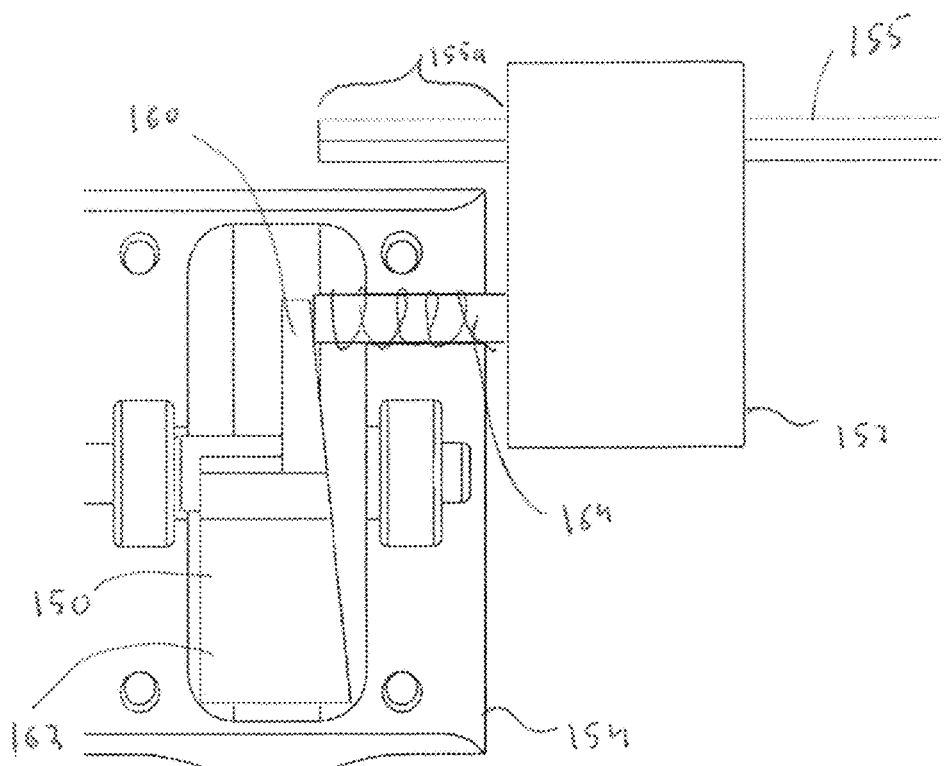
FIG. 14B is a view similar to FIG. 14A showing the rotating mass rotated to a second position wherein the sleeve and cannula are in the backward (proximal) position.

FIGS. 14A-14B illustrate an alternate embodiment having an offset end effector in a device that imparts a vibratory and reciprocal motion.

The device of FIGS. 14A-14B has a rotating eccentric mass 150 similar to rotating eccentric rotating mass 140 of FIG. 11A in that it imparts a vibratory motion and a reciprocating motion to the end effector. A connecting component or housing 152, shown schematically, is attached to the vibration actuator housing 154 which contains the eccentric rotating mass 140. Various ways to attach the housing 152 are contemplated. For example, the rod 164 connected to the housing 154 can piston in and out while restrained inside a channel within housing 154. To further reduce friction, this channel might include roller bearings. Additional railing mechanism parallel to the rod piston might further absorb the forces of driving the effector through the tissues and help with the alignment. The connection component 152 is offset from the vibration actuator housing 154 so the channel in component 152 which is dimensioned to receive the cannula 155 is radially spaced from the longitudinal axis of the vibration actuator shaft 157 and the motor shaft (not shown). In this manner, cannula 155 is radially offset from the longitudinal axis of the device. The region 155a of the cannula 155 is proximal of the distal end of housing 154 to thereby reduce the overall length.

When the disk like rotating mass 150 is rotated from the position of FIG. 14B where the narrower region 160 is adjacent or contiguous with the rod 164, the end effector (e.g., cannula) 155 is moved from the proximal position to the distal position of FIG. 14A as wider region 162 applies a distal force to the rod 164. Rotation of the eccentric mass 150 back to the position of FIG. 14B enables the end effector 155 to return to the proximal position. Note the rod 164 is constrained in a channel in the vibration actuator housing 154 by a spring 157. As in the embodiment of FIG. 11A, the eccentric rotating mass in addition to providing vibratory motion acts as a cam to impart reciprocal motion to the end effector.

Note the extent of excursion (distal movement) is determined by the shape, e.g., height or width, of the cam component so that the dimension of the cam can be different than that shown to increase or decrease the extent of distal movement. A seal that encloses the construct can be provided to maintain some lubricant.

Figure 15A:
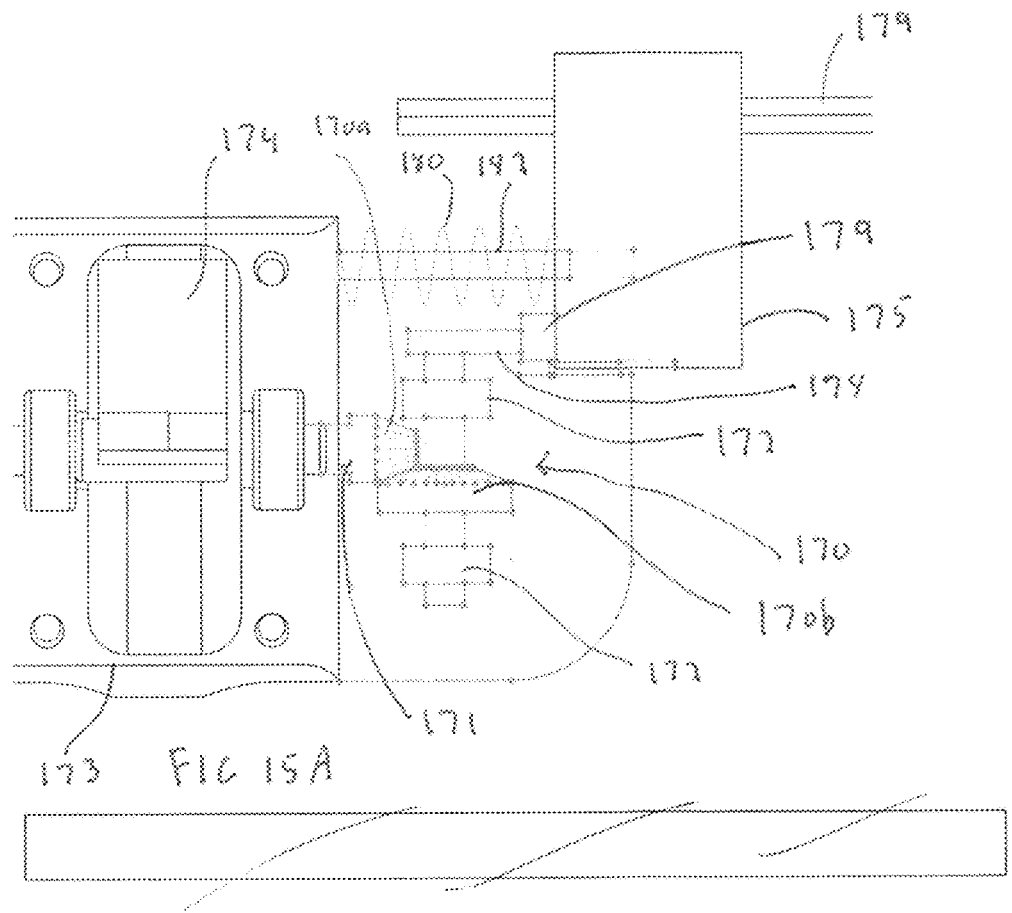
FIG. 15A is a side view of an alternate embodiment of the device of the present invention having an offset end effector and a gear mechanism, the device imparting a vibratory and reciprocal motion, and the cannula shown in the distal position.
Figure 15B:
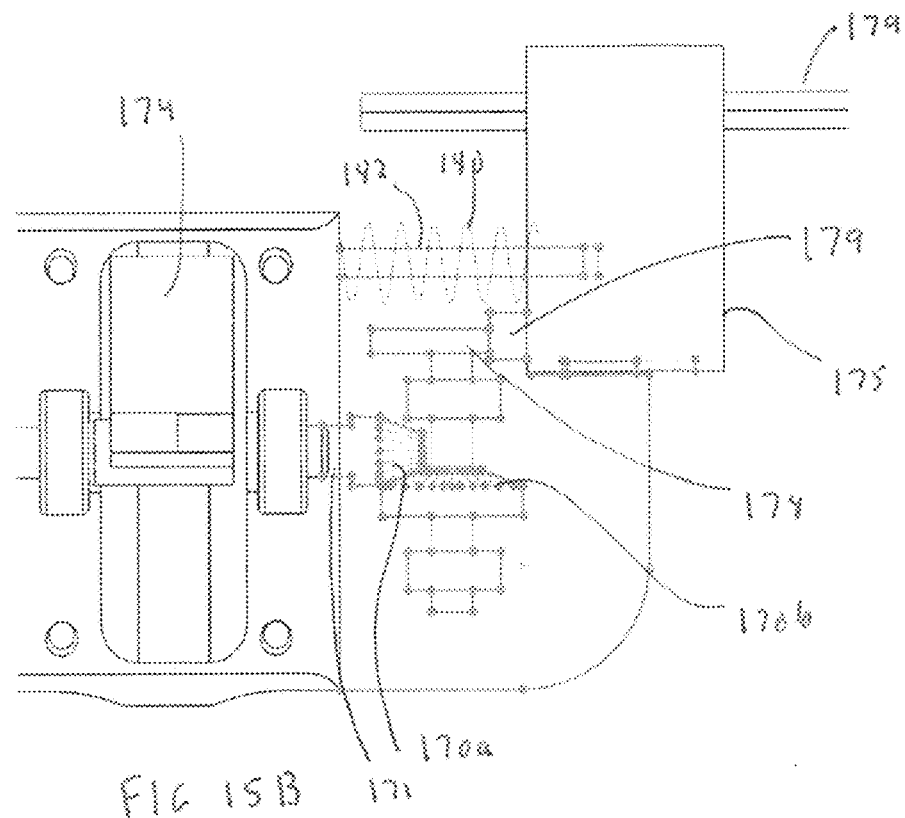
FIG. 15B is a view similar to FIG. 15A showing the cannula in the proximal position.

FIGS. 15A-17A illustrate alternate mechanisms for effecting reciprocal movement of the end effector. These devices can include the motor, dampening mechanism, bearings, etc. of device 10 of FIG. 1. In the embodiment of FIGS. 15A-15B, a gear mechanism 170 held by roller bearings 172 causes some de-multiplication and changes by 90 degrees the rotation axis to provide perpendicular cam rotation as rotation of the shaft 171 of the vibration actuator (eccentric mass) 174 about its axis rotates gear 170a of gear mechanism 170 which rotates gear 170b. Via this gear mechanism 170, rotation of the hemi-circular eccentric rotating mass 174 within vibration actuator housing 173 causes rotation of an ovoid cam 178 (your arrow 178 which causes the rod 179 to reciprocate according to the eccentricity of the cam, Thus, cam 178 provides a second smaller eccentric cam—which causes rod 178 to move in and out. Such reciprocation of the rod 178 causes the end effector 179, offset from the longitudinal axis of the device by connection component 175 (as in the embodiment of FIG. 14A) to reciprocate. Spring 180 and cylindrical channel 182 maintain stability and alignment of the end effector 179 and its clamping/connection mechanism 175. Rotation of eccentric rotating mass 174 imparts vibratory motion as described above in conjunction while rotation of the cam 174b imparts a reciprocal motion via the rod 178 through the gear mechanism 170. FIG. 15A illustrates the end effector 179 in the forward (distal) position and FIG. 15B illustrates the end effector in the inward (proximal) position.

Figure 16A:
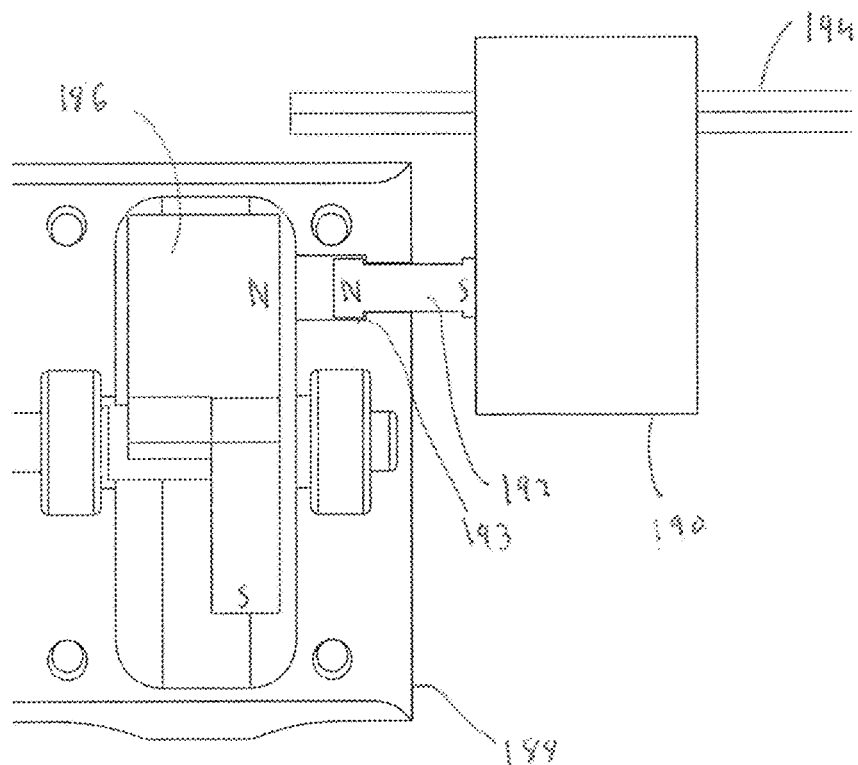
FIG. 16A is a side view of an alternate embodiment of the device of the present invention having an offset end effector and magnets for moving the end effector, the device imparting a vibratory and reciprocal motion, and the cannula shown in the distal position.
Figure 16B:
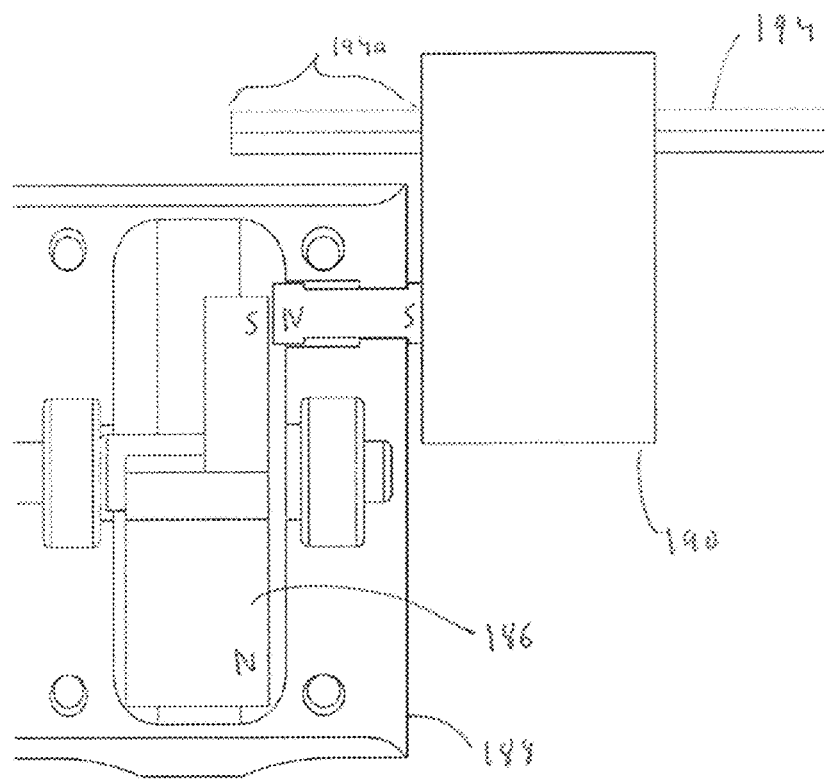
FIG. 16B is a view similar to FIG. 16A showing the cannula in the proximal position.

In the alternate embodiment of FIGS. 16A-16B, a magnetic system effects reciprocal motion. More specifically, the rotating eccentric mass 186 is also a magnet with a North Pole N on one hemi-circle and a South Pole S on the other hemi-circle. A piston-like magnet 192 constrained within a cylinder 193 also has North and South Poles. When the North Pole side of the rotating mass comes across the North Pole side of the piston magnet 192, it repels the piston thereby pushing it out which thereby pushes the end effector 194 out (distally) as shown in FIG. 16A. As the eccentric mass 186 rotates another half turn, the South Pole comes across the North Pole of the piston 192 to attract it in (proximally) and cause the end effector 194 to move back in (proximally) as shown in FIG. 16B. Note the end effector 194 is offset in the same manner as the end effector in FIG. 14A. The rotating eccentric mass 186 imparts both a vibratory and a reciprocal motion to the end effector as it rotates.

Figure 17A:
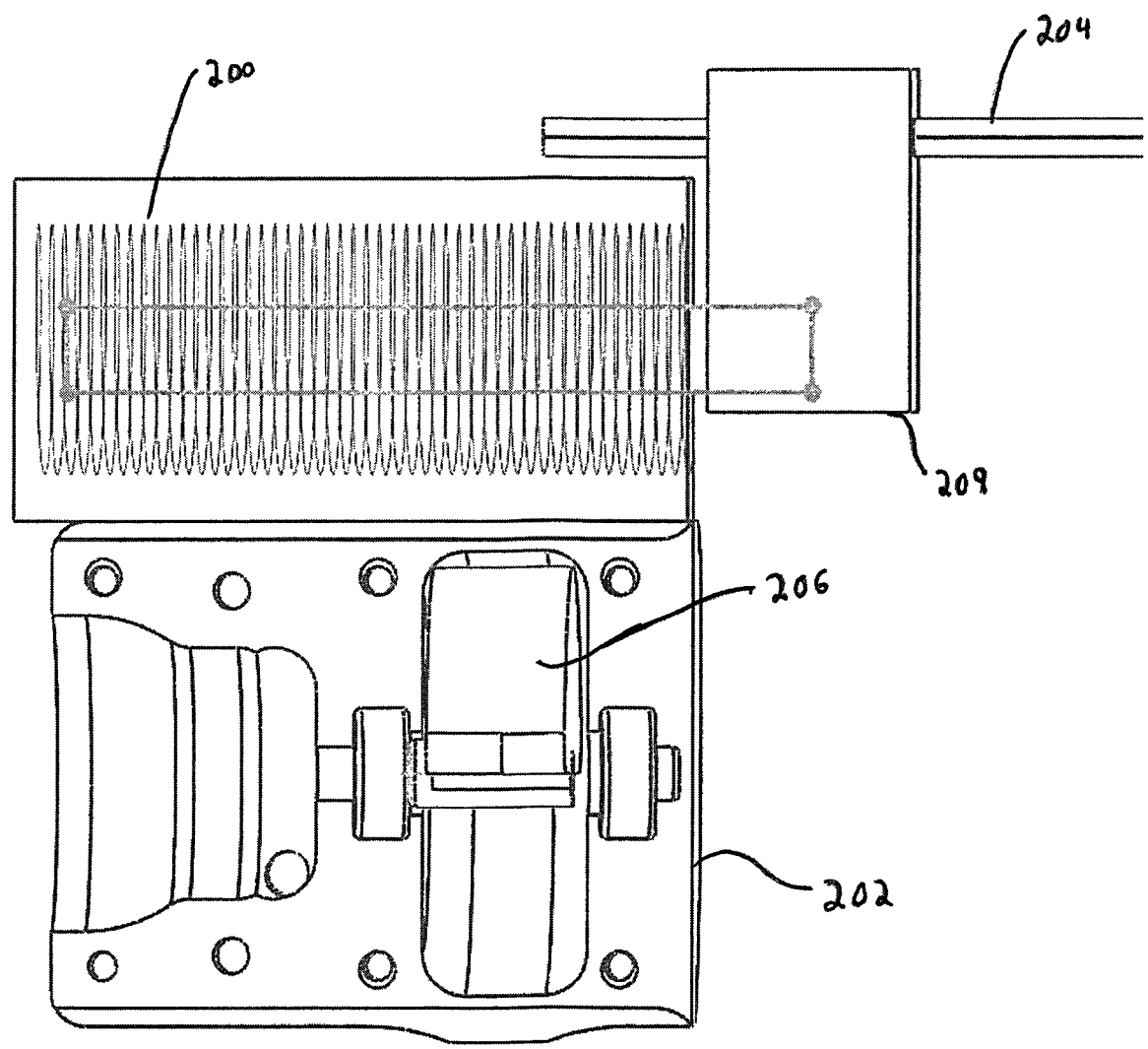
FIG. 17A is a side view of an alternate embodiment of the device of the present invention having an offset end effector and a solenoid mechanism for moving the end effector, the device imparting a vibratory and reciprocal motion, and the cannula shown in the proximal position.

In the alternate embodiment of FIG. 17A, an electrically driven solenoid 200 is connected to the vibration actuator 202 to cause the end effector 204 to move back and forth (reciprocate). Thus, the electro magnetic solenoid mechanism imparts reciprocal motion as the hemi-circular eccentric rotating mass 206 imparts vibratory motion as it rotates. Although the use of the solenoid adds the complexity of a separate electric set up to control the solenoid, it requires fewer moving parts and puts less strain on the existing moving parts. It also saves the flexible rotating shaft from additional torque load.

In alternate embodiments of either the sole vibration or vibration with reciprocal motion, the motor can be directly connected to the eccentric rotating mass and in some embodiments positioned in the housing for the vibration actuator such as in the housing 40 of FIG. 4. In such embodiments, the motor may vibrate. The vibration of the motor could be dampened by its clamping mechanism. Allowing the motor to vibrate may cause more wear and tear of the engine and shorten its life, but may reduce resources by eliminating the flexible rotating shaft. The dampening component in such embodiments can include coils such as the coil shaft 32 of FIG. 4 or rubber bumpers sleeves that shield the surgeon's gripping part of the hand piece from the vibration. In some of the embodiments wherein the motor is directly connected to the eccentric rotating mass, the rotating shaft spring need not be provided and a passive spring (coil) is provided to dampen vibration and protect the operator's hand.

The rotating mass can be designed to have an adjustable eccentricity in order to modulate the oscillating force. Moreover, a power control unit (microcontroller) could induce different vibration frequencies and different vibration amplitudes to provide different effects, both biologic and mechanical. When the vibration frequency resonates with the endogenous vibration frequency of the cannula, this can result in a harmonic vibration pattern that markedly increases the amplitude of the vibration and significantly widens the harvesting surface area compared to a device that achieves unidimensional harvesting, Thus, the device(s) of the present invention can be considered a three-dimensional harvester. Some advantages can include: i) efficiency in harvesting milliliters/minute/stroke; ii) selective harvesting of stromal vascular fraction; iii) efficiency in loosening and atraumatically re-arranging/re-orienting/reorganizing the extracelluar fibrovascular scaffold that gives shape to soft tissues and thus helps in re-shaping tissues whether by contracting them, expanding them or rendering them more malleable so that they can be molded; and/or iv) achieving other effects, such as local inflammation, induction of fibrosis collagen synthesis, blood flow (circulatory effect, both short and long term), capillary and nerve fibers disruption, or the like.

In some embodiments, an electronic control component includes a microcontroller to control the operation of the engine component. In some embodiments, the microcontroller sends electronic control signals to the engine component to start, stop, and adjust the speed and/power of the engine component. In some embodiments, the handheld component includes a user interface in communication with the microcontroller. The user interface may include input mechanisms, such as a touch screen, buttons, switches, keyboard, or a combination thereof, for an operator to control the operation of surgical handpiece. In some embodiments, the user interface displays the current vibration parameters to the operator, such as frequency, amplitude, power, speed of the motor, duration, and/or other parameters. The user interface may display a selection these parameters used in the current vibration procedure. The user interface may also display a selection of these parameters used in one or more previous vibration procedures.

In some embodiments, the mechanical vibration is continuously applied for a period of time. In some embodiments, the mechanical vibration is intermittently applied for a period of time. In some embodiments, the frequency, amplitude, and duration of the mechanical vibration delivered by the surgical handpiece may be manually adjusted by the operator or automatically adjusted according to a pre-programmed procedure saved in a non-transitory memory of the electronic control component.

Although the apparatus and methods of the subject disclosure have been described with respect to preferred embodiments, those skilled in the art will readily appreciate that changes and modifications may be made thereto without departing from the spirit and scope of the present disclosure as defined by the appended claims.

What is claimed is:

1. A vibrating hand held surgical instrument for loosening tissue of a patient comprising:
 a motor;
 a rotating drive shaft having a first end and a second end, the first end operatively connected to the motor;
 a vibration actuator including an eccentric rotating mass operatively connected to the drive shaft, the eccentric rotating mass remaining outside the patient, the eccentric rotating mass positioned in a proximal housing; and
 a cannula extending distally of the eccentric rotating mass, wherein the motor is configured to rotate the eccentric mass to cause the cannula to vibrate to loosen tissue, and the cannula is operatively connected to the vibration actuator and removable from the vibration actuator for interchangeability of the cannula, the cannula having a lumen extending therein;
 wherein the cannula has an angled proximal region within the proximal housing of the instrument, the angled proximal region extending at an angle to a longitudinal axis of the instrument, wherein the angled proximal region is distal of the motor, the lumen of the cannula extending through the angled proximal region and the proximal end of the cannula extending outside a side of the proximal housing to connect with an external fluid source.

2. The surgical instrument of claim 1, wherein the lumen is configured for one or both of providing injection or removing tissue from the patient.

3. The surgical instrument of claim 1, wherein the cannula and has one or more side openings at a distal region communicating with the lumen of the cannula.

4. The surgical instrument of claim 1, wherein the cannula has a connecting portion for connection to a suction source or an injection source, the connecting portion at an angle to a longitudinal axis of the cannula.

5. The surgical instrument of claim 1, wherein the proximal housing has a groove and a portion of the cannula extends into the groove and angles outwardly with respect to the groove.

6. The surgical instrument of claim 1, wherein the cannula has a hockey-stick configuration.

7. The surgical instrument of claim 1, wherein a tip of the cannula loosens an area of tissue wider than the cannula.

8. The surgical instrument of claim 1, further comprising a bearing on a proximal and distal side of the eccentric rotating mass to withstand lateral stresses and axial forces.

9. The surgical instrument of claim 1, wherein the eccentric rotating mass is hemi-disc shaped and rotates in a cavity in the proximal housing.

10. The method of claim 1, wherein the cannula has an inner wall and an outer wall defining a wall thickness between the inner wall and the outer wall, the cannula is the only cannula of the instrument and the outer wall of the cannula contacts the tissue.

11. A vibrating hand held surgical instrument for loosening tissue of a patient comprising:
 a handle configured to be held by a user;
 a motor;
 a rotating drive shaft having a first end and a second end, the first end operatively connected to the motor;
 a vibration actuator including an eccentric rotating mass operatively connected to the drive shaft, the eccentric rotating mass remaining outside the patient; and
 a cannula extending distally of the eccentric rotating mass, wherein the motor is configured to rotate the eccentric mass to cause the cannula to vibrate to loosen tissue, the cannula has an angled proximal portion spaced from the handle, the angled proximal portion extending at an angle to a longitudinal axis of the instrument and a distal portion of the cannula aligned with a longitudinal axis of the cannula, wherein the angled proximal region is in a housing containing the eccentric rotating mass, the housing separate and axially spaced from the handle to provide a gap therebetween.

12. The surgical instrument of claim 11, wherein the cannula has a lumen configured for one or both of providing injection or removing tissue from the patient.

13. The surgical instrument of claim 12, wherein the cannula and has one or more side openings at a distal region communicating with the lumen of the cannula.

14. The method of claim 11, wherein the angled proximal region of the cannula is distal of the handle.

15. A method for performing liposuction or loosening of soft tissue comprising:
   a) providing a hand held device having a hand-held part, a motor, a vibration actuator operatively connected to the motor and a cannula operatively connected to the vibration actuator, the vibration actuator positioned in a housing outside the patient and spaced proximally of a tissue contacting end of the cannula;
   b) actuating the motor to effect rotation of the vibration actuator to effect vibration of the cannula in tissue, wherein vibration is in multiple axes and provides true vibratory motion without oscillatory motion and the housing containing the vibration actuator is separate from the hand-held part of the device and axially spaced therefrom; and
   c) harvesting through the cannula fat dislodged from the tissue.

16. The method of claim 15, wherein the step of harvesting fat harvests fat from an area wider than the cannula during vibration of the cannula.

17. The method of claim 15, further comprising injecting through the cannula either one or both of a) during vibration of the cannula; and b) after vibration of the cannula.

18. The method of claim 15, further comprising harvesting and injecting through the cannula during vibration.

19. The method of claim 15, wherein the cannula is configured for lipografting.

20. The method of claim 15, wherein a proximal end of the cannula is distal of the hand-held part.

* * * * *